US012728050B2

(12) United States Patent
Shizukuishi

(10) Patent No.: US 12,728,050 B2
(45) Date of Patent: Sep. 8, 2026

(54) MEDICAL VEHICLES, CT DEVICES, AND DRIVING METHODS THEREOF

(71) Applicant: Makoto Shizukuishi, Sendai (JP)

(72) Inventor: Makoto Shizukuishi, Sendai (JP)

( * ) Notice: Subject to any disclaimer, the term of this patent is extended or adjusted under 35 U.S.C. 154(b) by 201 days.

(21) Appl. No.: 18/740,945

(22) Filed: Jun. 12, 2024

(65) Prior Publication Data

US 2024/0325219 A1 Oct. 3, 2024

Related U.S. Application Data

(63) Continuation of application No. 17/560,995, filed on Dec. 23, 2021, now Pat. No. 12,029,691, which is a (Continued)

(30) Foreign Application Priority Data

Jul. 9, 2019 (JP) ................................ 2019-127481
Sep. 11, 2019 (JP) ................................ 2019-165058
Apr. 13, 2020 (JP) ................................ 2020-071537

(51) Int. Cl.
*A61G 3/00* (2006.01)
*A61B 6/00* (2006.01)
(Continued)

(52) U.S. Cl.
CPC .............. *A61G 3/001* (2013.01); *A61B 6/035* (2013.01); *A61B 6/0407* (2013.01); *A61B 6/105* (2013.01);
(Continued)

(58) Field of Classification Search
CPC .... A61G 3/001; A61G 2210/50; A61B 6/035; A61B 6/0407; A61B 6/105; A61B 6/4482; A61B 6/56
See application file for complete search history.

(56) References Cited

U.S. PATENT DOCUMENTS 5,315,101 A 5/1994 Hughes et al.
5,336,879 A 8/1994 Sauer
(Continued)

FOREIGN PATENT DOCUMENTS

CN 102802532 A 11/2012
CN 104101615 A 10/2014
(Continued)

OTHER PUBLICATIONS

Monolithic CMOS Sensors for high energy physicsâChallenges and perspectives (Year: 2023).*
(Continued)

*Primary Examiner* — Uzma Alam
*Assistant Examiner* — Fani Polyzos Boosalis
(74) *Attorney, Agent, or Firm* — Harness, Dickey & Pierce, P.L.C.

(57) ABSTRACT

A vehicle includes a computed tomographic system (CT) including a CT gantry having an inner peripheral, and a subject window in a surface of the vehicle. The subject window is configured to be exposed to an exterior of the vehicle via a side face of the vehicle, such that the subject window is configured to enable a subject to enter or exit from the inner peripheral of the CT gantry in a body axis direction of the CT.

20 Claims, 13 Drawing Sheets

Related U.S. Application Data continuation-in-part of application No. PCT/JP2020/026699, filed on Jul. 8, 2020.

(51) Int. Cl.
*A61B 6/03* (2006.01)
*A61B 6/04* (2006.01)
*A61B 6/10* (2006.01)

(52) U.S. Cl.
CPC .............. *A61B 6/4482* (2013.01); *A61B 6/56* (2013.01); *A61G 2210/50* (2013.01)

(56) References Cited

U.S. PATENT DOCUMENTS

| | | | |
|---|---|---|---|
| 5,381,014 A | 1/1995 | Jeromin et al. | |
| 5,448,608 A | 9/1995 | Swain et al. | |
| 5,635,718 A | 6/1997 | DePuydt et al. | |
| 6,342,700 B1 | 1/2002 | Izumi et al. | |
| 6,384,396 B1 | 5/2002 | Mizuno et al. | |
| 6,906,332 B2 | 6/2005 | Tashiro et al. | |
| 8,659,148 B2 | 2/2014 | Tkaczyk et al. | |
| 9,314,220 B2 * | 4/2016 | Luhta | A61B 6/56 |
| 9,808,159 B2 | 11/2017 | Shizukuishi | |
| 9,943,275 B2 | 4/2018 | Shizukuishi | |
| 10,680,021 B2 | 6/2020 | Jacob | |
| 11,457,882 B2 | 10/2022 | Shizukuishi | |
| 11,723,613 B2 | 8/2023 | Shizukuishi | |
| 2012/0136196 A1 | 5/2012 | Foxall et al. | |
| 2015/0036786 A1 | 2/2015 | Katcha et al. | |
| 2017/0231843 A1 | 8/2017 | Thompson | |
| 2021/0153825 A1 | 5/2021 | Shizukuishi | |
| 2022/0151844 A1 | 5/2022 | Shizukuishi | |

FOREIGN PATENT DOCUMENTS

| | | |
|---|---|---|
| CN | 105960206 A | 9/2016 |
| CN | 104101615 B | 2/2017 |
| JP | S60-68767 A | 4/1985 |
| JP | S63-181369 A | 7/1988 |
| JP | H02-163968 A | 6/1990 |
| JP | H02-224746 A | 9/1990 |
| JP | H04-292149 A | 10/1992 |
| JP | H05-315581 A | 11/1993 |
| JP | H06-114047 A | 4/1994 |
| JP | H07-204192 A | 8/1995 |
| JP | H07-235652 A | 9/1995 |
| JP | H08-127282 A | 5/1996 |
| JP | H08-510883 A | 11/1996 |
| JP | H09-508549 A | 9/1997 |
| JP | H10-93061 A | 4/1998 |
| JP | H11-347023 A | 12/1999 |
| JP | 2000-022120 A | 1/2000 |
| JP | 2000-504410 A | 4/2000 |
| JP | 2000-278605 A | 10/2000 |
| JP | 2001-291877 A | 10/2001 |
| JP | 2002-600 A | 1/2002 |
| JP | 2002-090462 A | 3/2002 |
| JP | 2003-078827 A | 3/2003 |
| JP | 2007-151707 A | 6/2007 |
| JP | 2007-232438 A | 9/2007 |
| JP | 2011-147652 A | 8/2011 |
| JP | 2012-511988 A | 5/2012 |
| JP | 2012-118060 A | 6/2012 |
| JP | 2012-139602 A | 7/2012 |
| JP | 5027339 B1 | 9/2012 |
| JP | 5424371 B1 | 2/2014 |
| JP | 2015-107161 A | 6/2015 |
| JP | 2016-019110 A | 2/2016 |
| JP | 5970641 B2 | 8/2016 |
| JP | 6586550 B1 | 10/2019 |
| JP | 6820989 B1 | 1/2021 |
| JP | 6821074 B1 | 1/2021 |
| JP | 6842590 B1 | 3/2021 |
| JP | 6858317 B1 | 4/2021 |
| WO | 2000-26966 A1 | 5/2000 |
| WO | 2005/121725 A2 | 12/2005 |
| WO | 2010/070554 A1 | 6/2010 |
| WO | 2018-208668 A1 | 11/2018 |
| WO | 2020/137939 A1 | 7/2020 |
| WO | 2021/006166 A1 | 1/2021 |

OTHER PUBLICATIONS

CMOS Detector Staggered Array Module for Sub-Terahertz Imaging on Conveyor Belt System (Year: 2023).*

International Search Report for corresponding Application No. PCT/JP2020/026699, mailing date Sep. 24, 2020.

Chinese Office Action dated Oct. 17, 2024 for corresponding Chinese Application No. 202080041239.7, and English-language translation thereof.

* cited by examiner 61
71
Y
X
20
18
3
3S
52
100

60
3S
9-1
16-4
16-5
16-6
80
Z
70
5
18
61
X
22-1
16P
22-2
51
16-1
16-2
16-3
100
20
62
52
3

Y
61
61
Z
55-3
51
5
11
5
3
20
51
3S
7
5
Y
9-1
5
3S
X
55-1
62
100

65
53
20
5
51
51-2
3-1
5
55-1
3-2
300

Y
Z
310
67-1
57
5
20
h
51-2
3
d
51
3S
7
11
55-1

60
80
70
22-1
22-2
3S
16-4
16-5
16-6
18
67-1
5
51
16P
57
16-3
3
20
52
16-1
16-2
310
Z
X 57
67-2
57'
320
5
20
20'
51
3-1
3-3
55-1
3-3'
3-1'
59
59'
Y
Z

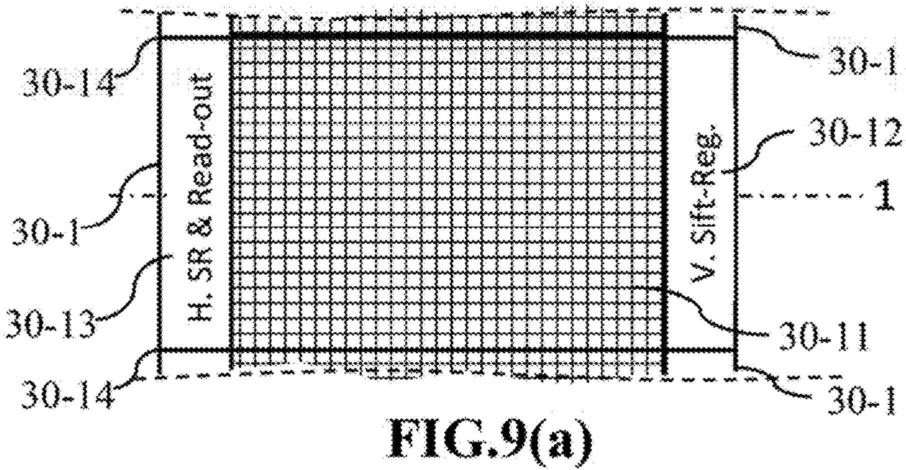
FIG.9(a)
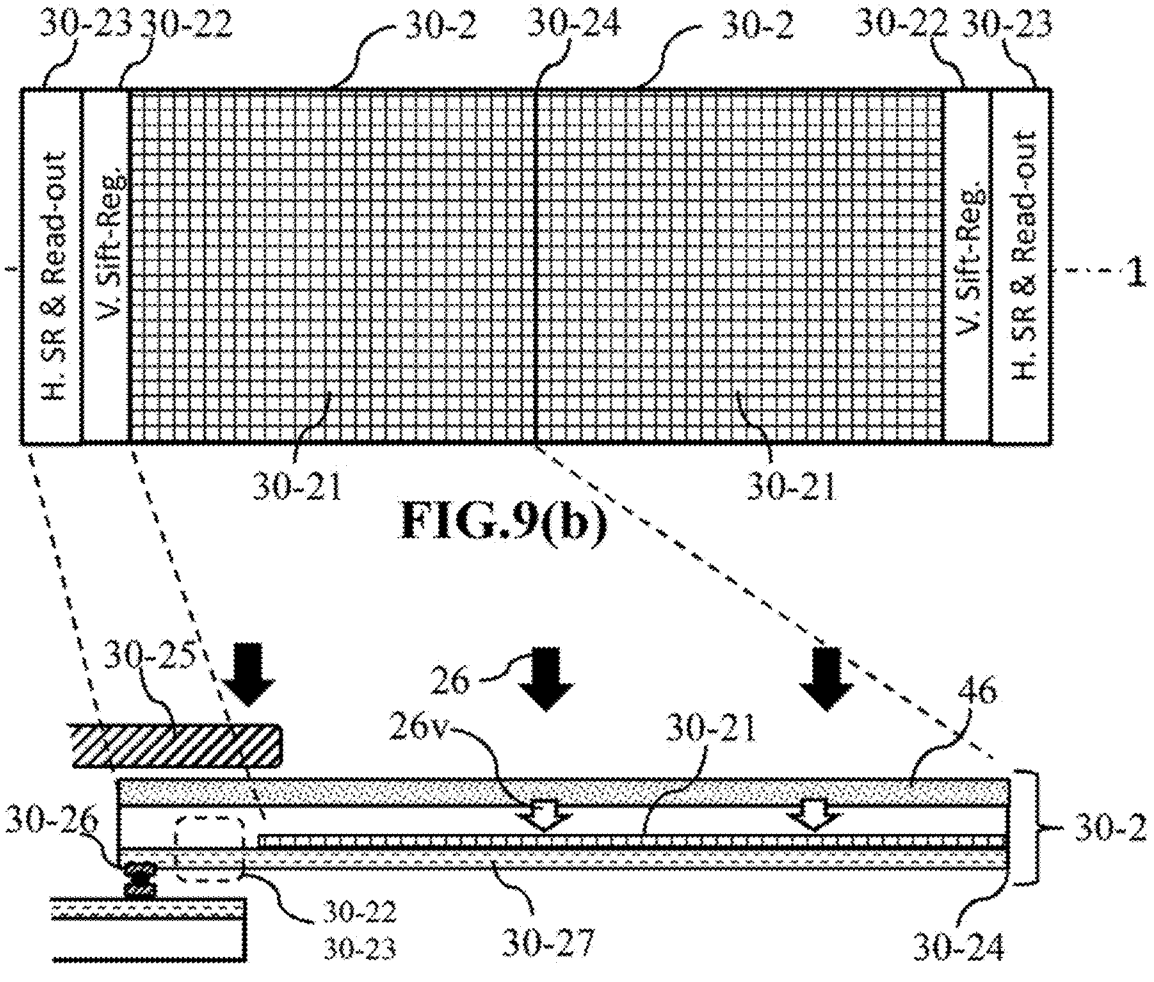
FIG.9(b)
FIG.9(c)

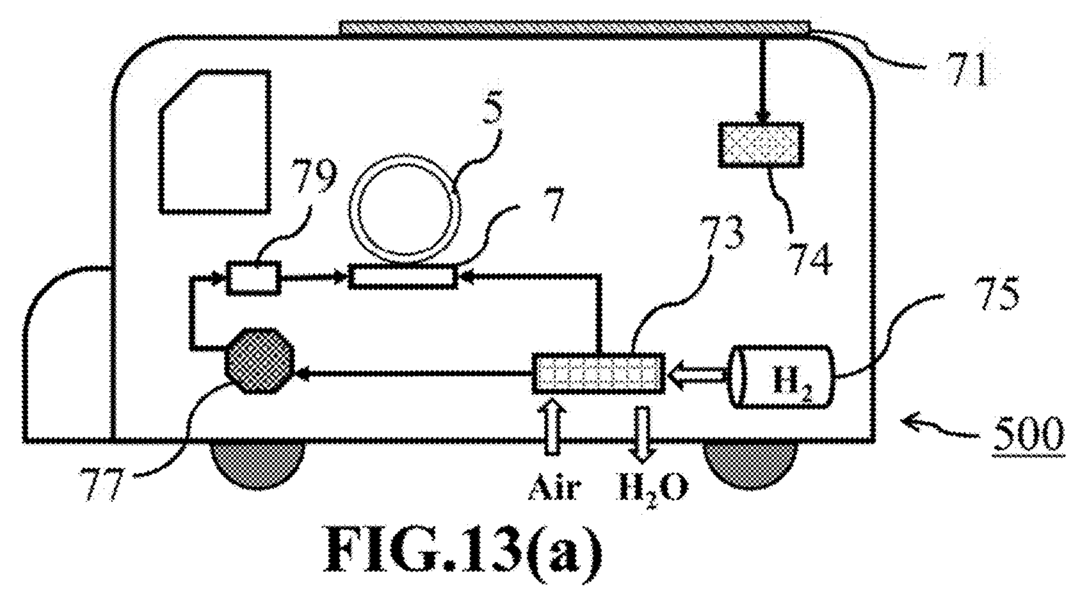
FIG.13(a)
FIG.13(b)
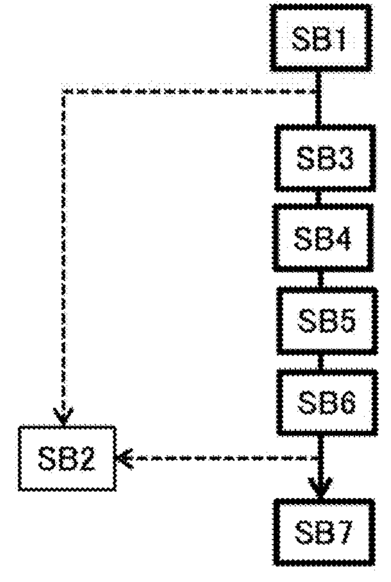
FIG.13(c)

MEDICAL VEHICLES, CT DEVICES, AND DRIVING METHODS THEREOF

CROSS-REFERENCE TO RELATED APPLICATIONS

This application is a Continuation of U.S. application Ser. No. 17/560,995, filed on Dec. 23, 2021, which is a Continuation-in-part of PCT/JP2020/026699 filed on Jul. 8, 2020, which claims priority to Japanese Patent Application No. 2019-127481 filed on Jul. 9, 2019, in the Japanese Patent Office (JPO), Japanese Patent Application No. 2019-165058 filed on Sep. 11, 2019, in the Japanese Patent Office (JPO), and Japanese Patent Application No. 2020-071537 filed on Apr. 13, 2020, in the Japanese Patent Office (JPO), the entire contents of each of which are incorporated herein by reference.

BACKGROUND

1. Technical Field

Example embodiments relate to medical vehicles having one or more computed tomographic (CT) systems, CT systems with smaller form factor and lower power consumption and driving methods thereof enabling high spatial, timing and energy resolution.

2. Related Art

An imaging apparatus, for example, an X-ray computed tomographic system (CT) comprises a gantry including a rotating part that rotates around an imaging target, a bed on which a subject is placed so as to pass through the inside of the gantry in the direction of the central axis of the rotation, a moving bed supporting member, and a slip ring around the rotating part enabling an electrical connection with an operation and monitoring console which reconstructs the subject image using the image data transferred via the slip ring. Inside the rotating part, a detector composed of a group of a large number of image pickup elements formed on multiple glass substrates, a circuit board for processing signals from the detector, an X-ray generating part at a position facing each other across an imaging object such as a subject, cooling fan, and a high-voltage power supply circuit are incorporated. A conventional CT is a large, heavy, and expensive image diagnostic equipment. In addition to the costs of the building for the CT including the cost of a large power supply and air conditioning systems, also maintenance cost to keep the CT always with optimal performance and conditions cause a heavy financial burden. Therefore, various difficulties arise in moving the CT to change its installation location or using the CT outdoors. Vehicles equipped with X-ray inspection devices are known, however enlarging of the vehicle size itself is unavoidable, and required inspection time becomes long because each subject enters the vehicle to have an inspection one by one. As a result, it has been difficult for many subjects to undergo image inspections efficiently.

SUMMARY

Mobile medical vehicles equipped with X-ray equipment have the primary purpose of performing screening tests for many subjects. If any suspicious findings are pointed out by the screening test, it is necessary to go to a specialized hospital or laboratory later and undergo a detailed examination again. However, for the elderly or those who live in depopulated areas, it is extremely time-consuming, physical, or financially burdensome to have a detailed examination again. It may be necessary to reduce the installation space in addition to reducing the size and weight of the CT itself when a CT is used in a transportation means such as a vehicle. A stroke area for horizontal movement of the bed should be secured. Further, a waiting or preparation space for subjects may be required since each subject enters the vehicle and lays down on the bed, respectively. As a result, the examination time per person becomes long and difficult to perform CT examinations on many subjects efficiently. If the space provided for a CT will be reduced, the room (e.g., area, volume, etc.) for mounting some more medical devices within a medical vehicle may be expanded. These are problems to be solved to reduce or minimize the stroke area and the space provided to the subject and to enable rapid examination processing when using a CT.

In recent years, the spread of infectious diseases caused by new viruses has become a global problem. Diagnostic imaging equipment such as a CT, for example, is indispensable for early detection of initial symptoms of pneumonia. Compared with the conventional chest X-ray examination, a CT is expected as a means for identifying pneumonia and other infectious diseases at their initial stages immediately since the CT has higher examination accuracy. At the same time, the issue of how to protect medical professionals from these unknown infectious diseases has also been raised. For example, there is a substantial risk for nurses, examination technicians, or the like getting infected when CT examinations are performed on a large number of subjects who may be infected with a new virus or the like. As described above, in addition to the increasing and speeding up the number of examinations, it is also an issue to be solved how to protect medical staff and the like.

CT size and weight should be reduced when the CT is used in transportation means such as a vehicle. An X-ray source, a detector, detector signal processing circuits, an X-ray source drive control circuit, and a cooling fan, for example, are built in a rotating part inside a gantry. However, the X-ray source, the X-ray source drive control circuit, the cooling fan are heavy weight units. It is also a problem to be solved to reduce or minimize the harmful effects such as vibrations and noises caused by the moment of inertia or heavy rotating parts, which are placed on the circumference inside the gantry and rotates at a rotating speed of 0.5 revolutions per second or more.

The increase in the amount of power required by the CT and in the amount of power required by air conditioning equipment to deal with the heat generated by the equipment such as a CT has become a problem. Usually, a single CT may require a power supply unit of 50 KVA, for example. It is an indispensable task to reduce the amount of power used by a CT and the amount of power used for air conditioning equipment to cope with heat generation of the equipment in view of global warming due to $CO_2$ emissions. It may be also necessary to cope with operational conditions when operating the CT by batteries, or outdoors such as in a remote location without a stable commercial electrical power supply. Further, it should be an issue to suppress the temperature rise due to the heat generated from the CT in the inspection room or inside the medical vehicle to reduce the power consumption and energy loss of the CT itself. The detector, the detector signal processing circuit, the X-ray source, the X-ray source drive control circuit, and the cooling fan inside the rotating portion are heavy weight (e.g., relatively heavy in weight). There is a problem that moment of inertia, vibrations due to the rotations of heavy objects rotating at a speed of 1 to 2 revolutions per second on a circle with a diameter of 80 cm or more, and noises may be generated. The moment of inertia is proportional to the weight of the rotating part and the square of the radius of gyration. Conventionally, a resistor called a regenerative resistor is used to dissipate the electrical energy generated by the kinetic energy of the moment of inertia to the outside as Joule heat. As a result, the temperature of the CT will rise, and the load on the cooling device may be increased.

In order to supply power or read out an output signal from a detector or the like, transmission and reception of a signal, or transmission or reception of power is performed by a mechanical contact means called a slip ring. For the electrical connection by the slip ring, it is necessary to keep the rotation speed low and to reduce the number of output signal lines from the detector. For reducing the number of signal lines, serialization of the parallel signal read through the slip ring is adopted. However, when a large amount of image data is serially transmitted, the transmission frequency rises. It may become necessary to develop some custom semiconductor elements such as a high-speed line buffer element, for example. With an increase in the transmission frequency, more power consumption and heat generation by the CT cannot be avoided. In recent years, the slice width of CTs are being widened so that the wide area can be exposed by a single X-ray pulse irradiation. As a result, in addition to the weight of the gantry increasing, the size of the X-ray generator used in a CT may increase. The light receiving area (or the number of slices) in the body axis direction is expanded, which increases the light receiving area of the detector used or the total number of pixels, requiring further increases in the speed and the capacity of data transmission and high-speed real-time recording. A data processing speed exceeding 1 gigabyte/second is required when the number of slices of 64 may be used, for example. In order to record a large amount of data in real time at high speed, it is necessary to use a plurality of hard disks such as RAID (Redundant Arrays of Independent Disks) in combination, where the recording speed may be limited up to 800 Mbytes per second, for example. As used herein, the “body axis direction” may refer to “body axis direction” as the term is used in the medical CT field. A “body axis direction” as used herein may be interchangeably referred to as a “CT bed moving direction,” a “CT gantry moving direction,” or the like.

The above-mentioned electric power feeding to the X-ray source or the like may cause a problem. Based on the slice width being increased, the X-ray source may increase in size and the amount of current supplied to the X-ray source drive circuit and a high-voltage generation circuit has tended to increase as an X-ray tube current increase. Therefore, the slip ring of the CT needs to flow a large amount of current by sliding the brush on the slip ring, which may cause heat generation and seizure on the contact surface. Therefore, maintenance such as surface polishing of the slip ring and brush electrode, or regular replacement of these parts are required. To use a CT in a vehicle or the like, it is necessary to be able to easily inspect, repair, and replace faulty parts at each destination in addition to making the bed and the gantry part smaller and lighter. The periodic maintenance load of the CT should be also reduced. Further, in recent years, concerns about X-ray exposures have increased as increasing the opportunities for using X-ray CT and the like. Reducing the total amount of X-ray exposure of subjects, CT operators, radiologists, or nurses in CT examinations is also a problem to be solved.

It may not be possible to use a stable commercial power source depending on the natural conditions or on the area where medical activities are carried out depending on the situation in which a medical vehicle is used. Therefore, it may be required for the vehicle to have its own stable power supply means (e.g., power source, power supply, power supply unit, etc.) and sufficient power supply capacity for conducting medical activities. In addition, it should be considered that medical vehicles are used outdoors where measures may be taken to reduce, minimize, or prevent effects of fluctuations in temperature and humidity, air pollution, and dust upon medical activities. Medical vehicles may be used in evacuation centers such as local gymnasiums, hotel lobbies, inside tents, and the like. Such a medical vehicle itself should not generate noise or emit harmful exhaust gas from the power supply unit during their medical activities. In addition to the above-mentioned problems such as miniaturization of the medical vehicle itself and low power consumption, it is also required to provide a clean power source that enables stable long-term operation without generating vibrations or noises.

Some example embodiments provide medical vehicles having a CT with reduced size and cost. In a medical vehicle having a CT, a stroke area required by the CT should be reduced, minimized, or eliminated to reduce the size of the medical vehicle or to expand the space for mounting other medical devices in the medical vehicle. A medical vehicle equipped with a CT has a subject window near the left-side surface, the right-side surface, or the rear side surface of the medical vehicle, which may be an opening defined to extend between an exterior and an interior of the medical vehicle and which is configured to enable introducing or carrying out the subject (e.g., a person, a human body, animal body, etc.) or a bed on which the subject is placed. The medical vehicle also has a tubular subject protector that penetrates the inner peripheral portion (also referred to herein as the “inner peripheral,” “inner periphery,” or the like) of the gantry. Further, the other end of the tubular subject protector is closed so that the subject protector may block outside air (e.g., air from an ambient environment that is external to the medical vehicle from entering inside (e.g., entering the interior of) the medical vehicle.

A medical vehicle according to some example embodiments of the inventive concepts, for example, a medical vehicle equipped with a CT has a subject window on a vehicle side surface. In some example embodiments, the subject window is circular as viewed from the subject body axis direction. The central axis of the circular subject window may correspond to the central axis of the inner peripheral (e.g., inner periphery, inner diameter, etc.) of the CT gantry. The diameter of the subject window may be larger than the diameter of the inner peripheral of the CT gantry, and the diameter of the subject window may be smaller than the diameter of the outer diameter (e.g., outer peripheral) of the CT gantry. In some example embodiments, the steering wheel is attached at the right-hand side of the vehicle and the subject window is formed near the left side face of the vehicle, or the steering wheel is attached at the left-hand side of the vehicle and the subject window is formed near the right-side face of the vehicle. The CT may be placed behind a driver’s and a passenger’s seats when the body axis direction of the CT is oriented at right angles to the straightforward direction of the vehicle. Further, the passenger’s seat may become the CT operator’s seat.

In some example embodiments, the CT gantry may move in a subject body axis direction while inspecting a subject. Further, a cradle may be provided at a particular (or, alternatively, predetermined) position of the CT to retract the movable CT gantry. In some example embodiments, the CT gantry may be fixed near the side face of the vehicle and the bed may move in a subject body axis direction while inspecting a subject. Two subject windows are formed on the right-side face and the left-side face of the vehicle and the centrals axes of the right and left-side subject windows may correspond to the central axis of the inner peripheral of the CT gantry when the body axis direction of the CT is oriented at right angles to the straightforward direction of the vehicle. Further, the CT gantry may be located at the center of the vehicle in the body axis direction. In some example embodiments, the subject window may be formed on the rear-side face of the vehicle when the body axis direction of the CT is oriented at the straightforward direction of the vehicle.

As mentioned above, the CT used in the medical vehicle may include a tubular shaped subject protector which penetrates the inner peripheral portion of the CT gantry, and the end portion of the subject protector meets the subject window. In some example embodiments, the shape of the subject protector in the subject window portion viewed from the body axis direction is circular. The diameter of the subject window is larger than the diameter of the inner peripheral of the tubular shaped subject protector, and the diameter of the subject window is smaller than the diameter of the outer diameter of the CT gantry. Further, a funnel shaped subject protector is provided to be continuously formed between the side face of the vehicle and the tubular shaped subject protector. The other end of the tubular shaped subject protector inside the vehicle is closed. In some example embodiments the tubular subject protector and two funnel shaped subject protectors are continuously formed from the right-side face of the vehicle to the left side face of the vehicle in case of above-mentioned vehicle with two subject windows. With these configurations, the inflow and outflow of outside air between the inside (e.g., interior) and the outside (e.g., exterior) of the medical vehicle may be blocked.

In some example embodiments, an entrance space between the subject window and the side face of the vehicle is provided and the opening area of the entrance space is larger than the opening area of the subject protector as viewed from the body axis direction of the CT. A subject (person, human body, animal body, or the like) can sit on or lie down on the bed inside the gantry personally and then the entrance space may play the role of a small front chamber or waiting room.

In some example embodiments, a medical vehicle equipped with a CT where a light source (e.g., X-ray generator), a light source drive control circuit, a detector at a position facing the light source across the central axis, a detector control and signal processing circuit for the output signals from the detector, a semiconductor image memory for recording the output signals and a rechargeable battery (also referred to a secondary battery, such as a lithium-ion battery) for driving these circuits are provided inside the rotating part of the gantry. In some example embodiments, any of the rechargeable battery, the light source, the detector, and the semiconductor image memory in the rotating part of the medical vehicle have a cartridge structure or detachable cartridge form. In some example embodiments, the light source is an X-ray light source where the electron beam generating portion is comprised of carbon nanostructures.

In some example embodiments, a medical vehicle equipped with a CT where a light source, a light source drive control circuit, and a rechargeable battery for driving these are provided in the rotating part inside the gantry, and a plurality of detectors are mounted on the entire circumference of the inner circumference of the annular fixed part surrounding and concentric with the rotating part. An opening, through which the light emitted from the light source to expose the light receiving surface of the detector, is formed to face the light source in opposite side in between the rotation center of the rotating part.

A medical vehicle according to some example embodiments of the inventive concepts, for example, the CT used in the medical vehicle has a gantry having a rotating part that rotates about a body axis direction, a gantry table on which the gantry is placed, a control part for processing and displaying image data obtained from the gantry, and an operating part of the CT. In addition, the CT has a drive means for moving the gantry in the direction of the central axis. Further, the rotating part has a light source, a light source drive and control circuit, and the rotating part interface, and the gantry table has a host interface. The rotating part interface and the host interface are face to face at a particular (or, alternatively, predetermined) position within the range of the gantry movement. In some example embodiments, the particular (or, alternatively, predetermined) position is at the end of the gantry moving range. In some example embodiments, the rotating part interface and the host interface are close to each other and face to face in the vertical direction. In some example embodiments, the rotating part interface and the host interface are close to each other and face to face in the central axis direction. The rotating part interface and the host interface are mechanically contacted to be electrically connected at a particular (or, alternatively, predetermined) position. In some example embodiments, the rotating part interface and the host interface are close to each other at a particular (or, alternatively, predetermined) position and are electrically connected to each other in a contactless manner also referred to herein interchangeably as a wireless manner by an interaction of an electromagnetic field.

A medical vehicle according to some example embodiments of the inventive concepts, for example, the CT used in the medical vehicle has a driving means inside the gantry for moving the gantry in the central axis direction. Further, a drive motor for rotating the rotating part is provided inside the gantry. A subject protector for preventing the subject or the object to be measured from meeting the moving gantry, or reducing the likelihood of the subject or the object to be measured meeting the moving gantry, is provided on the gantry table along the moving direction of the gantry. A cradle is provided at a particular (or, alternatively, predetermined) position above the gantry table, and a host interface is located at the cradle. Further, the cradle has a test probe used for testing or calibrating the rotating part, or a holding means for holding a correlation sample. In some example embodiments, the cradle has a holding mechanism for holding and fixing the rotating part at the particular (or, alternatively, predetermined) position, or a cooling mechanism for cooling the rotating part.

In some example embodiments, a lithium-ion battery is used as the above rechargeable battery. As the image memory, a large-capacity semiconductor memory, for example, such as a non-volatile memory like a NAND flash memory may be used. The light source is an X-ray light source or a near infrared (NIR) light source, for example. In some example embodiments, the light source is an X-ray light source which employs a carbon nanostructure for an electron beam generating part. The detector is preferably a silicon-based semiconductor sensor, and an analog to digital (AD) conversion circuit is also formed on the silicon-based semiconductor sensor. In some example embodiments, the detector may be a photomultiplier tube type sensor, an avalanche photodiode (APD) type sensor, or a photon counting type sensor. In some example embodiments, the radiation shielding optical fiber plate may be provided on the detector, or the radiation scintillator may be further laminated on the radiation shielding optical fiber plate. In some example embodiments, the silicon semiconductor detector is a CMOS solid-state image sensor of a back-illuminated type, and further, X-ray shielding member is placed above the integrated circuits such as horizontal and vertical scanning circuits and signal readout circuits to protect from X-ray damage or reduce X-ray damage.

A medical vehicle according to some example embodiments of the inventive concepts, for example, the CT used in the medical vehicle has a plurality of induction coils which are arranged along the annular part of the rotating part and has permanent magnets which are arranged along the fixed part of the gantry that surrounds the rotating part so that the N poles and the S poles are alternately placed. In some example embodiments, an energy recovery brake circuit converting the kinetic energy of the rotating part into electrical energy is connected to the in the induction coils. An electric double layer capacitor may be provided in the energy recovery brake circuit. A driving method using the energy recovery brake circuit is as follows. Starting the rotating part rotation, then imaging of the subject by X-ray irradiation begins. The digital data obtained from the detector array is recorded in the image memory in real time manner. After the imaging is completed, the rotational kinetic energy of the rotating part generates a counter electromotive force in the induction coils and is recovered as electrical energy to charge the capacitor or the rechargeable battery. Next, the data recorded in the image memory is read from the rotating part interface via the host interface. In parallel, the rechargeable battery is charged, and the series of the driving sequence is completed to set the standby state. A modified above example of the driving method using the energy recovery brake circuit is as follows. If the rotation speed of the rotating part during the CT imaging step is defined as n1, and the rotation speed of the rotating part of non-CT imaging step is defined as n2, then the rotation speed n2 of the rotating part is increased more than n1 (n2>n1) to charge the rechargeable battery.

The rotation of the rotating part in the gantry may be continued for a while due to the moment of inertia even after the imaging step. The rotating part is interlocked with the drive motor being installed by a timing belt. Therefore, an electromotive force is generated in the motor when the rotating part continues to rotate by the moment of inertia. As described above, by connecting the regenerative resistor, the generated electric power is dissipated to the surroundings as Joule heat.

A medical vehicle according to some example embodiments of the inventive concepts, for example, in order to suppress such Joule heat, the CT has a structure to reduce the moment of inertia which rotates the drive motor. The rotating part inside the gantry used in the CT of the medical vehicle comprises two parts where a timing belt is attached to one rotating part and the other rotating part is mechanically linked with the one rotating part by a ratchet or clutch structure. Claws are attached around the one rotating part, and they are caught in grooves on the inner circumference of the other rotating part when the one rotating part rotates clockwise transmitting torque to the other rotating part. On the contrary, when the one rotating part rotates counterclockwise, the claws cannot transmit torque getting over the grooves on the inner circumference of the other rotating part which will idle. Depending on the shapes of the claw and the groove, the rotation direction with or without torque transmission can be changed. After the end of imaging, the interlocking of the one rotating part and the other rotating part is canceled, and the inertia moment of the other rotating part is not transmitted to the drive motor. The moment of inertia of one rotating part is reduced by separating the other rotating part because the moment of inertia is proportional to the mass of the rotating part. The mass of the one rotating part can be further reduced by mounting a component having a large mass such as a light source and a detector on the other rotating part. Further, it may be desirable to set the radius of the one rotating part being smaller than the radius of the other rotating part since the moment of inertia increases in proportion to the square of the radius of gyration. With this configuration, it becomes possible to suppress the electromotive force generated in the drive motor connected to the one rotating part via the timing belt by releasing the other rotating part from the one rotating part after the imaging is completed. Further, the moment of inertia of the rotating part can be recovered and reused as an electric energy by providing the energy recovery brake circuit in the other rotating part having a larger moment of inertia than the one rotating part, or in the fixed part surrounding the rotating part. The ratchet structure may be a kind of a clutch structure such as a meshing clutch, a friction clutch, a centrifugal clutch, and an electromagnetic clutch.

Further, a plurality of ring-shaped electrodes (so-called a slip ring) are provided around the annular shape of the other rotating part, and a plurality of terminals performing electrical contacts with the plurality of the ring-shaped electrodes are provided on the fixed part surrounding the outer periphery of the other rotating part. In some example embodiments, the CT is such that the rotational moment of the one rotating part is smaller than the rotational moment of the other rotating part. In some example embodiments, the CT is such that the weight of the one rotating part is smaller than the weight of the other rotating part. In some example embodiments, the CT has a light source, a light source drive control circuit, a detector, a detector drive circuit, and a processing circuit for the output signal of the detector inside the other rotating part. Further, the CT has a rechargeable battery and a rotating part interface inside the other rotating part, and a host interface for transmitting and receiving signals or power to and from the rotating part interface on the inner circumference of the fixed part surrounding the rotating part. In the CT driving method when the ratchet structure is used, after the one rotating part rotates in the direction in which torque can be applied to the other rotating part, imaging by X-ray irradiation starts. The digital data obtained from the detector array is recorded in the image memory in real time manner. When the rotational torque of one rotating part decreases or stops after the end of imaging, the other rotating part is released from the coupling with the one rotating part and idles. By the energy recovery brake circuit in the other rotating part, the rotational kinetic energy generates a counter electromotive force in the induction coil and recovers it as an electrical energy to charge the capacitor or the rechargeable battery. The rotational movement of the other rotating part may subsequently be decelerated. After the rotation of the other rotating part is stopped, the data recorded in the image memory is read out from the rotating part interface via the host interface. In parallel, the rechargeable battery is charged and then a series of sequences are completed to enter the standby state.

The CT used in the medical vehicle has cartridge formed light source, detector, image memory, or rechargeable battery in the rotating part inside the gantry. Further, openings of individual cartridge storage portions are formed on the outer circumference of the rotating part where the light source, the detector, the image memory, or the rechargeable battery having cartridge forms can be inserted or removed from the inside of the rotating part toward the normal direction of the outer circumference of the rotating part perpendicular to the central axis of the gantry in the direction of the central axis of the rotating portion with respect to the cartridge storage portion. In some example embodiments, the CT used in the medical vehicle has cartridge formed light source, detector, image memory, or rechargeable battery in the rotating part inside the gantry. Further, openings of individual cartridge storage portions are formed on the side face of the rotating part where the light source, the detector, the image memory, or the rechargeable battery having cartridge forms can be inserted or removed in the direction of the central axis in the rotating part. In some example embodiments, the first X-ray generator and the second X-ray generator are provided, and the first detector array and the second detector array are placed on the opposite sides of these X-ray generators, respectively via the central axis. The first detector array or the second detector array may be arranged at positions shifted in the direction of the central axis. Further, the first X-ray generator and the second X-ray generator may emit X-rays at the same time or with a different timing. Furthermore, different X-ray tube voltages (or wavelengths) may be applied to the first X-ray generator and the second X-ray generator.

The CT used in the medical vehicle has a wireless interface on the rotating part, on the CT controlling part, on the fixed part of the gantry, on the gantry table, or on the cradle side in order to transmit and receive a control signal to control the movement of the gantry in the body axis direction, and to operate the imaging process inside the gantry. Further, the CT used for the medical vehicle has a structure in which two gantry parts are mounted on a gantry table. The cradle may have a donut-shaped hollow structure through which a subject or a bed can pass. The medical vehicle may combine plurality of gantries such as an X-ray CT examination gantry, a positron emission tomography (PET) examination gantry, or a near-infrared diffused light imaging gantry.

The medical vehicle has a fuel cell battery using hydrogen for driving the CT. In some example embodiments, the medical vehicle is an electric vehicle powered by a fuel cell (e.g., fuel cell battery) and the fuel cell drives a CT. The driving method of the medical vehicle is such that the rechargeable battery used inside the rotating part of the CT may be charged by the energy recovery brake circuit which converts the kinetic energy during deceleration of the moving medical vehicle into electrical energy while the rotating part is stationary.

According to the present inventive concepts, it has become easy to miniaturize a medical vehicle equipped with CT by reducing, minimizing, or eliminating the stroke region required by the CT. It has become easier to secure the space required when using CT, for example, the stroke for horizontal movement of the bed, outside the medical vehicle, and quick and efficient inspection becomes possible. Even if a stable commercial power source cannot be obtained, it has become possible to continue medical activities by using its own stable power supply means. Using a clean power source, stable and long-time CT operation is possible without generating noise or emitting harmful exhaust gas caused by the power supply. Therefore, medical activities in a closed or semi-closed space such as a gymnasium which may become an evacuation center, a hotel lobby, or the inside of a tent becomes easier. Comparing with conventional inspection equipment in large-scale hospitals, the power consumption of the CT can be significantly reduced and the power supply unit for the CT may become one-tenth or less, for example. The spread of the medical vehicles equipped with the CT may contribute to the reduction or prevention of global warming and to achieve Sustainable Development Goals (SDGs) even in a medical or healthcare field. Imaging diagnosis by the CT may be useful not only for early detection of serious diseases such as cancer, heart disease, and cerebrovascular disease but also some other lesions may be observed in the images other than above purposes. By utilizing AI and high-speed communication technic, it becomes possible to detect such various abnormalities that may occur in the human body from a wide range of viewpoints even in remote areas without overlooking them. By using the medical vehicle of the present inventive concepts and combining a high-speed communication method such as 5G and image diagnosis utilizing AI (artificial intelligence), a one-stop medical service can be realized even in a remote place or a disaster site.

BRIEF DESCRIPTION OF THE DRAWINGS

The above and other features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 1(*b*) is a plan view of a medical vehicle looking down from a Y-axis direction, according to some example embodiments.

FIG. 1(*c*) is a cross-sectional view showing an arrangement of the CT of a medical vehicle when viewed from a rear portion (X-axis direction) of the medical vehicle, according to some example embodiments.

FIG. 1(*d*) is a cross-sectional view of a CT mounted on a medical vehicle as viewed from a Z-axis direction, according to some example embodiments.

FIG. 2(*b*) is a plan view of a medical vehicle as viewed from a Y-axis direction, according to some example embodiments.

FIG. 2(*c*) is a cross-sectional view illustrating an arrangement of a CT of a medical vehicle viewed from a rear portion (X-axis direction) of the medical vehicle, according to some example embodiments.

FIG. 3(*b*) is a cross-sectional view of a medical vehicle, particularly illustrating an arrangement of a CT of the medical vehicle viewed from a rear (X-axis direction), according to some example embodiments.

FIG. 3(*c*) is a plan view of a medical vehicle looking down from a Y-axis direction, according to some example embodiments.

FIG. 3(*d*) is a cross-sectional view of a medical vehicle, particularly illustrating an arrangement of a CT of the medical vehicle viewed from a rear portion (X-axis direction), according to some example embodiments.

FIG. 4(*b*) is a plan view of a medical vehicle viewed from a rear portion (X-axis direction), according to some example embodiments.

FIG. 4(*c*) is a plan view of a medical vehicle looking down from a Y-axis direction, according to some example embodiments.

FIG. 5(*b*) is a plan view of a CT looking down from a Y-axis direction, according to some example embodiments.

FIG. 5(*c*) is a plan view of a main part of a CT viewed from a Z-axis direction, according to some example embodiments.

FIG. 6(*b*) is a block diagram showing a circuit configuration of a wireless power feeding part in a non-contact interface part, according to some example embodiments.

FIG. 7(*b*) is a circuit block diagram showing a detector and peripheral circuits of the detector, according to some example embodiments.

FIG. 7(*c*) is a circuit block diagram inside of a rotating part, particularly showing an X-ray generating portion and a high voltage drive circuit, according to some example embodiments.

FIG. 8(*b*) is a cross-sectional view taken from an X-axis direction showing another gantry structure suitable for a CT, according to some example embodiments.

FIG. 8(*c*) is an enlarged view of a portion A surrounded by a broken line A as shown in FIG. 8(*a*), according to some example embodiments.

FIG. 8(*d*) is a plan view of the opening viewed from a direction of an X-ray source showing the opening being formed in a rotating part, and the part of a sensor unit located in a fixed part is visible through the opening, according to some example embodiments.

FIG. 9(*a*) is a plan view of a CMOS-type solid-state detector unit which is a modified example of the detector unit as shown in FIG. 8(*d*), according to some example embodiments.

FIG. 9(*b*) is a plan view of CMOS type solid-state sensor units, which are suitable modified examples of a sensor unit, are arranged so that the light receiving regions are close to each other, according to some example embodiments.

FIG. 9(*c*) is an enlarged view of a cross-sectional structure of the CMOS type solid-state sensor unit shown in FIG. 9(*b*), according to some example embodiments.

FIG. 10(*b*) is a plan view of a CT seen from a body axis direction, according to some example embodiments.

FIG. 10(*c*) is an enlarged view of the portion B surrounded by the broken line of the CT as shown in FIG. 10(*a*), according to some example embodiments.

FIG. 10(*d*) is a cross-sectional view of rotating parts of a CT as viewed from an X-axis direction, according to some example embodiments.

FIG. 10(*e*) is a plan view of the rotating part of a CT viewed from a body axis direction, according to some example embodiments.

FIG. 11(*b*) and FIG. 11(*c*) are partially enlarged views of electromagnetic induction arrangements between the outer circumference of the rotating part of a CT and the inner circumference of the gantry surrounding the rotating part of the CT as indicated by the broken line portion 39 in FIG. 11(*a*), according to some example embodiments.

FIG. 11(*d*) is a circuit block diagram showing the energy recovery brake circuit inside the rotating part of a CT, according to some example embodiments.

FIG. 12(*b*) is a partially enlarged view showing the ratchet mechanism in the rotating parts and of a CT as shown in FIG. 12(*a*), according to some example embodiments.

FIG. 12(*c*) is a flowchart for explaining a method of driving a CT having a gantry using the ratchet structure shown in FIGS. 12(*a*) and 12 (*b*).

FIG. 12(*d*) is a plan view of a gantry of a CT viewed from the Z-axis direction, according to some example embodiments.

FIG. 13(*a*) is a block diagram showing an electrical power supply arrangement in a medical vehicle, according to some example embodiments.

FIG. 13(*b*) is a schematic view showing a medical vehicle, according to some example embodiments.

FIG. 13(*c*) is a flowchart showing an operation of a medical vehicle and operation steps of a CT of the medical vehicle, according to some example embodiments.

DETAILED DESCRIPTION OF EXAMPLE EMBODIMENTS

Figures 1A, 1B, 1C, 1D:
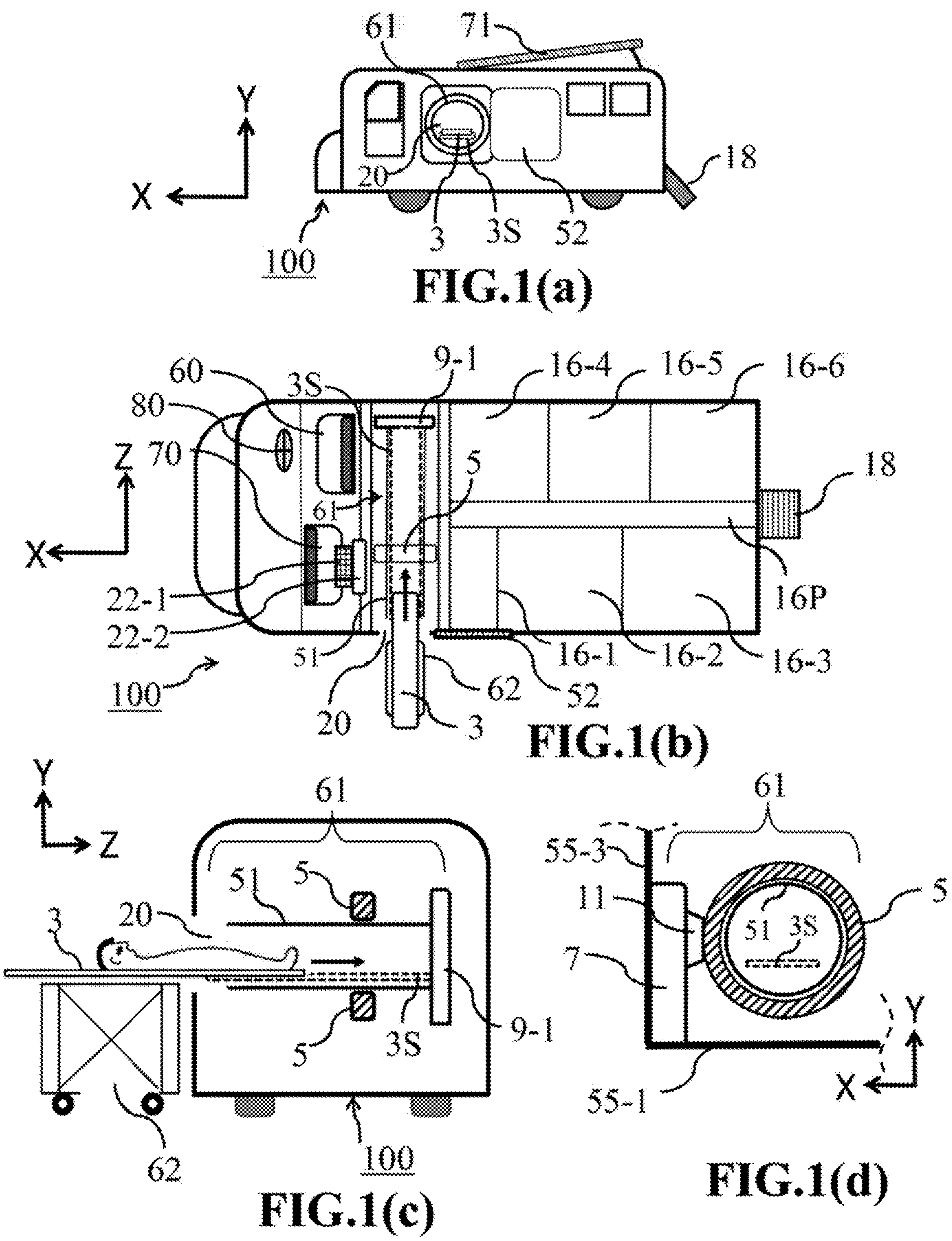
FIG. 1(*a*) is a side view of a medical vehicle as viewed from a Z-axis direction, according to some example embodiments.

Detailed example embodiments are described herein. However, specific structural and functional details described herein are merely representative for purposes of describing example embodiments. Example embodiments may, however, be embodied in many alternate forms and should not be construed as limited to only some example embodiments set forth herein.

Accordingly, while example embodiments are capable of various modifications and alternative forms, example embodiments of the inventive concepts are shown by way of example in the drawings and will herein be described in detail. It should be understood, however, that there is no intent to limit example embodiments to the particular forms described, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected to", "coupled to", or "on" another element, it may be directly connected to, directly coupled to, or directly on the other element, or intervening elements may be present. In contrast, when an element is referred to as being "directly connected to," "directly coupled to", or "directly on" another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

It will be understood that elements and/or properties thereof (e.g., structures, surfaces, directions, or the like), which may be referred to as being "perpendicular," "parallel," or the like with regard to other elements and/or properties thereof (e.g., structures, surfaces, directions, or the like) may be "perpendicular," "parallel," or the like or may be "substantially perpendicular," "substantially parallel," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In some example embodiments of the inventive concepts, the straight traveling direction of the vehicle is defined as the X axis, the height direction or the vertical direction of the vehicle is defined as the Y axis, and the horizontal direction with respect to the traveling direction orthogonal to the X axis and the Y axis is defined as the Z axis. Medical vehicles may include medical examination vehicles performing diagnostics, mobile hospitals having hospital functions, examination vehicles for non-human subjects such as a freight inspection by airport customs or forensic medicine, and rescue vehicles or ambulances used in the cases of disasters and emergencies.

The medical vehicle 100 according to some example embodiments will be described below with reference to FIGS. 1(*a*) to 1(*d*).

FIG. 1(*a*) is a side view of a medical vehicle 100 according to some example embodiments as viewed from the Z-axis direction. The medical vehicle 100 includes a computed tomographic (CT) system, also referred to herein simply as a CT, shown in FIG. 1(*a*) as CT 61. A subject window 20 is formed near the side face of the medical vehicle 100, through which a subject such as a human body, animal body, or the like, being placed on a bed 3 can be directly carried into the gantry portion (e.g., gantry 5) of the CT 61.

As shown in FIG. 1(*a*), the subject window 20 may be an opening in the side face (e.g., an opening formed in the side face) that extends between an exterior of the medical vehicle 100 and an interior of the medical vehicle 100. In some example embodiments, the subject window 20 is configured to establish communication between the inner peripheral part of a gantry of the CT 61 and an exterior of the medical vehicle 100 and thus enable a subject to enter the inner peripheral portion of the gantry portion of the CT 61 from an exterior of the medical vehicle 100 through the subject window 20 or to exit the inner peripheral portion of the gantry portion of the CT 61 to the exterior of the medical vehicle 100 through the subject window 20. It will be understood that in some example embodiments (e.g., as shown in at least FIGS. 3(*b*) and 3(*d*) as described further below) the subject window 20 may be an opening in a surface in an interior of the medical vehicle that may be exposed to an exterior of the medical vehicle via a space (e.g., entrance space 57 shown in FIG. 3(*b*)) that is at least partially defined by one or more surfaces within the interior of the medical vehicle, where the interior of the medical vehicle is a volume space at least partially defined by some or all side faces of the medical vehicle. It will be understood that a side face of a medical vehicle as described herein may be an outer face or surface of the vehicle that at least partially defines the boundary between the interior and exterior of the medical vehicle and thus at least partially defines a volume space within the medical vehicle that is the interior of the medical vehicle. The subject window 20 may be aligned with a body axis direction (e.g., body axis direction of the CT 61, body axis direction of the CT gantry 5, etc.), for example the central axis of the subject window 20 may be paraxial and/or coaxial with a central axis of the inner peripheral part of the gantry 5. As a result, the subject window 20 may be configured to enable a subject to enter or exit the inner peripheral portion of the gantry portion of the CT 61, from or to an exterior of the medical vehicle 100 through the subject window 20, along (e.g., in parallel or substantially in parallel with) the body axis direction (e.g., body axis direction of the CT 61, body axis direction of the CT gantry 5, etc.).

In view of at least the above, the subject window 20 of some example embodiments may be understood to be an opening defined by and/or formed in a surface that is configured to be exposed to an exterior of the medical vehicle via a side face of the medical vehicle such that the subject window 20 is configured to enable a subject to enter the inner peripheral of a CT gantry of a CT of a medical vehicle in a body axis direction (e.g., body axis direction of the CT 61, body axis direction of the CT gantry 5, etc.) from an exterior of the medical vehicle (e.g., enter or exit the inner peripheral of the CT gantry in the body axis direction of the CT in relation to the exterior of the medical vehicle) through the subject window 20. It will be understood that the surface that is configured to be exposed to the exterior of the medical vehicle via a side face of the medical vehicle may be the side face of the medical vehicle itself, which may be an outer face or surface of the medical vehicle that is directly exposed to an exterior of the medical vehicle, as shown in at least FIGS. 1(*a*)-1(*c*). The surface that is configured to be exposed to the exterior of the medical vehicle via a side face of the medical vehicle may be a surface such as an interior surface within an interior of the medical vehicle that is configured to be exposed to an exterior of the medical vehicle via a further opening in the side face and a space defined within the interior of the medical vehicle between the subject window and the side face, as shown in at least FIGS. 3(*b*)-3(*d*).

As used herein, a "body axis direction," including "body axis direction of the CT," "body axis direction of the CT gantry," "body axis direction of the subject," or the like may refer to "body axis direction" as the term is used in the medical CT field. A "body axis direction" as used herein, including "body axis direction of the CT," "body axis direction of the CT gantry," "body axis direction of the subject," or the like may be interchangeably referred to as a "CT bed moving direction," a "CT gantry moving direction," or the like. For example, in the example embodiments shown in FIGS. 1(*a*)-1(*d*), FIGS. 2(*a*)-2(*c*), and FIGS. 3(*a*)-3(*d*), the body axis direction extends in the Z-axis direction. In another example, in the example embodiments shown in FIGS. 4(*a*)-4(*c*), the body axis direction extends in the X-axis direction.

In FIG. 1(*a*), the inner peripheral part of the gantry of the CT 61 (labeled as gantry 5 in FIG. 1(*b*), also referred to interchangeably herein as a CT gantry) is shown. The body axis direction of the gantry portion of the CT 61 is perpendicular to the X-Y plane. In some example embodiments, the central axis of the inner peripheral part of the gantry 5 corresponds to the central axis of the circular shaped subject window 20. For example, the central axis of the inner peripheral part of the gantry 5 may be coaxial with and/or may be the same axis as the central axis of the circular shaped subject window 20. The subject window 20, in some example embodiments, may be understood to include an opening that extends through the side face of the medical vehicle 100 and/or is formed in the side face of the medical vehicle 100 such that the subject window is configured to enable a subject to enter or exit from an inner peripheral of a gantry 5 of the CT 61 in a body axis direction (e.g., a body axis direction of the gantry 5, a body axis direction of the CT 61, a body axis direction of the subject, etc.). Further the bed 3 on which the subject is placed, shifts (e.g., translates) onto the bed supporting member 3S, then an imaging step (e.g., an imaging operation) is performed (e.g., performed at least in part by the CT 61) while the gantry 5 is moving in the Z-axis direction as will be described later. In some example embodiments, the CT 61 may be used to take an image by a fixed gantry 5 while the subject is moving in the Z-axis direction. In some example embodiments, as will be described later, a sliding door 52 for shielding (e.g., covering) the subject window 20 (e.g., to reduce or prevent communication of objects, dust, fluids, etc. between the vehicle interior and vehicle exterior through the subject window 20) may be mounted on the side face. The medical vehicle 100 is equipped with a solar panel 71 to utilize natural energy like solar power to serve as a power supply for the medical vehicle 100 (including for example the CT 61 included therein), and stairs 18 for entering and exiting the medical vehicle 100. While the subject window 20 is shown as being circular, it will be understood that the subject window 20 may be non-circular in some example embodiments (e.g., rectangular, or a shape of any polygon).

FIG. 1(*b*) is a plan view of the medical vehicle 100 viewed from the Y-axis direction. The body axis direction of the CT 61 is oriented at right angles to (e.g., oriented perpendicular to) the X axis or the straightforward direction of the medical vehicle 100 (e.g., a direction of a longitudinal axis of the medical vehicle 100), and the CT 61 is placed behind a driver's 60 and a passenger's 70 seats. In some example embodiments, the diameter of the subject window 29 may be larger than the diameter of the inner peripheral of the CT gantry 5, and the diameter of the subject window 20 may be smaller than the diameter of the outer diameter (e.g., the outer peripheral) of the CT gantry 5. The CT gantry 5 moves in a body axis direction of the CT gantry 5 (e.g., moves in relation to the medical vehicle 100, moves in relation to other portions of the CT 61 including the gantry table 7, etc.) while the subject is stationary inside the CT 61 (e.g., stationary in relation to the CT 61, the medical vehicle 100, etc.). A cradle 9-1 is mounted at the other side of the subject window 20 (e.g., is located at an opposite side of the interior of the medical vehicle 100 from the subject window 20, for example as shown in FIG. 1(*c*)) as described in detail below. A driver's seat 60, a passenger seat 70 and a steering wheel 80 are provided in front of the medical vehicle 100. The passenger seat 70 can be rotated towards a backward direction (e.g., reversed from facing the +X direction to facing the −X direction) to face the CT 61, for example to be used as a CT operator's seat. Restated, the passenger seat 70 may be configured to be a CT operator seat for a CT operator of the CT 61 and thus may be configured to enable a CT operator to operate the CT 61. In some example embodiments, the backrest of the passenger's seat 70 may be reversed to become the CT operator's seat. Based on the CT operator using the passenger's seat to operate the CT 61 to perform the CT operation, no additional space for the CT operator to operate the CT 61 to perform the CT operation is required inside the medical vehicle 100. In some example embodiments, the driver's seat 60 and the steering wheel 80 are placed on the right side (e.g., attached to the medical vehicle 100 at a right of the medical vehicle 100), the passenger's seat 70 is located on (e.g., located at) the left side of the medical vehicle 100, and the subject window 20 is formed near (e.g., extends through, is formed in, etc.) the left side face of the medical vehicle 100, such that the side face of the medical vehicle 100 through which the subject window 20 may be exposed to the exterior of the medical vehicle 100 is the left side face of the medical vehicle 100. In some example embodiments, the passenger's seat 70 may be located on the right side (e.g., attached to the medical vehicle 100 at a right side of the medical vehicle 100) and the subject window 20 is formed near the right-side face of the medical vehicle 100, such that the side face of the medical vehicle 100 through which the subject window 20 may be exposed to the exterior of the medical vehicle 100 is the right side face of the medical vehicle 100, when the driver's seat 60 and the steering wheel 80 are placed on the left side of the medical vehicle 100 (e.g., attached to the medical vehicle 100 at a left side of the medical vehicle 100). An operation and control part, also referred to herein interchangeably as a control unit 22-1, and a display monitor 22-2 are provided at the backside of the passenger's seat 70 which will become the CT operator's seat. In some example embodiments, including any of the example embodiments herein, the display monitor 22-1 may include a display device including a display panel screen, such as a Light Emitting Diode (LED) display screen, an Organic Light Emitting Diode (OLED) display screen, or the like. The control unit 22-1 and the display monitor 22-2 are communicatively coupled to each other, such that the display monitor 22-2 is configured to display images based on signals generated at the control unit 22-1 and transmitted to the display monitor 22-2. The control unit 22-1 is communicatively coupled (also referred to herein as electrically coupled) to at least a data processing unit. In some example embodiments, including any of the example embodiments herein, the control unit 22-1 includes, is included in, and/or implements the data processing unit as described herein. A tomographic image reconstructed by an imaging circuit and software in the data processing unit in response to an imaging operation being performed by some or all of the CT 61 may be displayed on the display monitor 22-2.

The medical vehicle 100 may include some separate rooms such as a data processing and a power supply room 16-1 which may include the above-mentioned data processing unit, other testing equipment room 16-2, a biochemical analyzing room 16-3, a consultation room 16-4, a waiting room 16-5, a dressing room 16-6, and a cabin passage 16P, for example. Using a simple mobile bed 62 called a stretcher, a subject laying on the bed 3 can be carried onto the upper part of the bed supporting member 3S of the CT 61 through the subject window 20 formed on the vehicle side face of the medical vehicle 100. In some example embodiments, as will be described later, a cradle 9-1 is provided. The cradle 9-1 is a part that stands upright from the floor surface, wall surface, or pedestal for example, and provides a space in which the gantry 5 can stand by and provide a host interface being electrically coupled to a rotating part interface of the rotating part inside the gantry 5 as will be described later. A sliding door 52 for shielding the subject window 20 is provided in case for the CT 61 not being used, and/or when the medical vehicle 100 is moving. As described above, since the stroke region required by the CT 61 is not always necessary inside the medical vehicle 100 but outside the medical vehicle 100, the medical vehicle 100 can be smaller in size, or the space inside the vehicle (e.g., at least some of the volume space of the interior of the medical vehicle 100) can be used for other purposes effectively. As will be described below in detail, there are one or more light sources such as an X-ray source unit (e.g., an X-ray generator) rotating around the body axis direction inside the gantry 5. The tomographic image reconstructed by an image drawing circuit and software in the data processing unit is displayed on the display monitor 22-2. As described in detail below, a wired or wireless electrical connection may enable transmitting and receiving electrical signals or power between a rotating part and a fixed part in the gantry 5, or between a rotating part and the gantry fixed part. A robust and precise controllable subject movement bed is not required because only the gantry 5 moves in the Z-axis direction during the imaging step while the subject is stationary on the bed 3. Therefore, the medical vehicle 100 itself can be easily reduced in size and weight. Further, even if the image scanning speed in the body axis (Z axis) direction of the gantry 5 is increased, physical or mental loads and anxieties of the subject can be reduced.

FIG. 1(*c*) is a cross-sectional view of a main part of the medical vehicle 100, particularly when the CT 61 is viewed from the rear of the vehicle in the X-axis direction. The bed 3 on which the subject is placed is carried into the CT 61 from the subject window 20. The stretcher 62 may hold the bed 3, or the bed supporting member 3S may be provided with the CT 61 to hold the subject more stably. As described above, the gantry 5 has a rotatable light source (e.g., an X-ray generator) inside the gantry and takes a tomographic image of the subject while moving in the Z-axis direction. The gantry 5 moves along the subject. A tubular shaped (e.g., tube shaped, cylindrical, etc.) subject protector 51 is configured to penetrate the inner peripheral portion of the gantry 5 to prevent the subject from contacting with the moving gantry 5 as the gantry 5 moves along (e.g., moves in relation to) the subject, or reduce the likelihood of the subject contacting the moving gantry 5 as the gantry 5 moves along (e.g., moves in relation to) the subject. The diameter of the subject window 20 may be larger than the diameter of the inner peripheral of the subject protector 51, and the diameter of the subject window 20 is smaller than the diameter of the outer diameter (e.g., outer peripheral) of the CT gantry 5 in the body axis direction of the CT 61. The end portion of the subject protector 51 may meet (e.g., may be proximate to, may extend at least partially into, etc.) the subject window 20. Further, as described later, the cradle 9-1 is attached to the subject protector 51 on the opposite side of the subject window 20, that is, at the other end of the moving range of the gantry 5 (e.g., an opposite side of the moving range of the gantry 5 in relation to the subject window 20). The cradle 9-1 may perform electrical and/or mechanical coupling with the gantry 5. In FIG. 1(*c*), the subject (person) is carried into the CT 61 from the lower body side, however, the subject can be also carried into the CT 61 from the head side instead. In many cases, the examination target is the upper body portion of the subject such as the head and internal organs, and it may not be always necessary to image the whole body of the subject. Therefore, the dimension of the CT 61 in the Z-axis direction can be shortened to about 1 m (meter) for example, and the space (e.g., volume space) occupied by the CT 61 in the medical vehicle 100 (e.g., within the interior of the medical vehicle 100) can be reduced.

FIG. 1(*d*) is an enlarged view of a main part of the CT 61 as viewed from the Z-axis direction. The outer shape of the subject protector 51 is circular because the subject protector 51 is located at the inner peripheral portion of the gantry 5. The gantry 5 moves above (e.g., moves in relation to) the gantry table 7. A gantry moving carriage 11 is attached to the gantry 5. In some example embodiments, the gantry table 7 is attached to the side surface 55-3 of the medical vehicle 100, but it may be attached on the floor surface (55-1) of the medical vehicle 100 instead as described later.

Figures 2A, 2B, 2C:
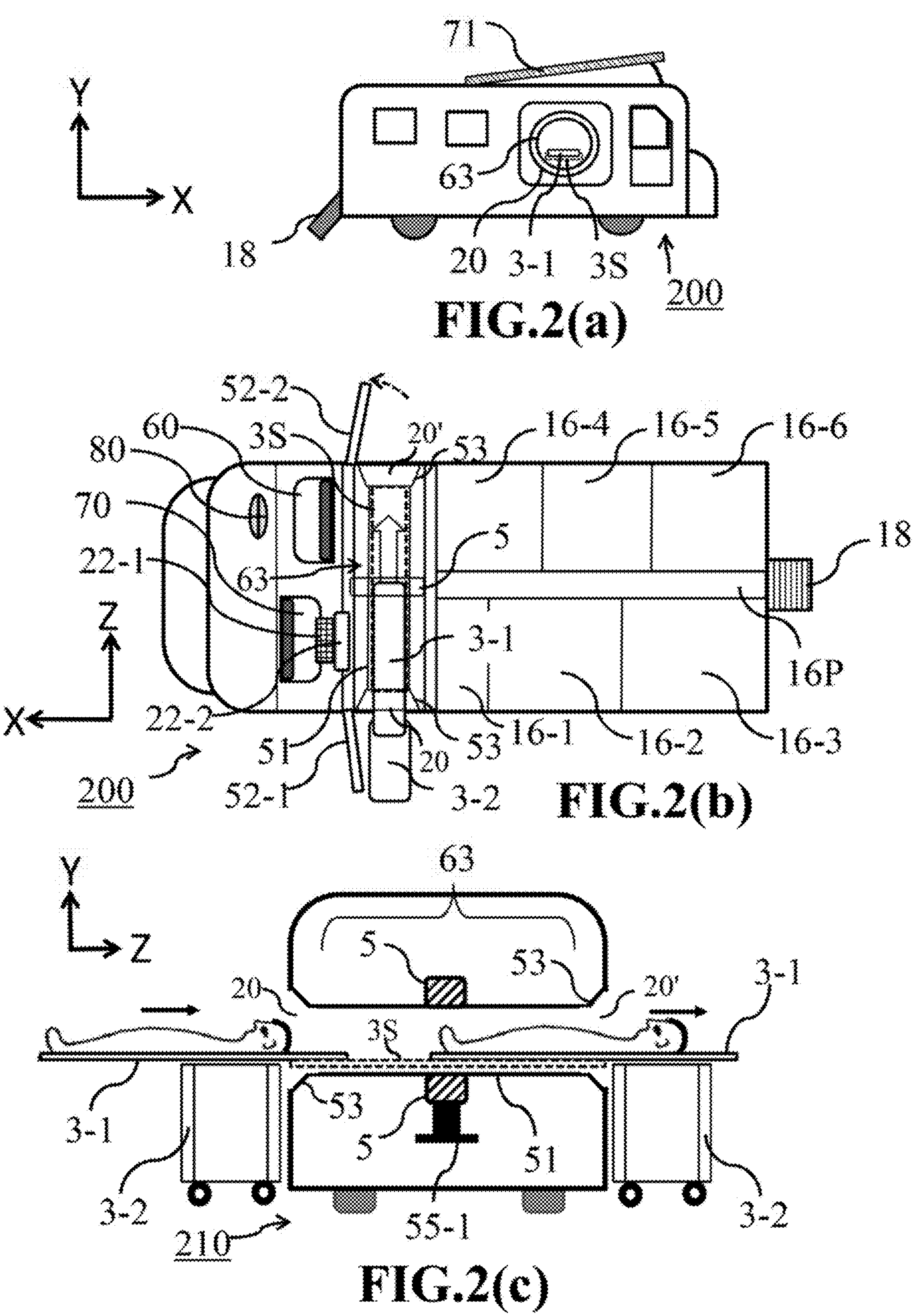
FIG. 2(*a*) is a side view of a medical vehicle viewed from a Z-axis direction, according to some example embodiments.

With reference to FIGS. 2(*a*) to 2(*c*), the medical vehicle 200 according to at least one some example embodiments and the medical vehicle 210 according to some example embodiments will be described below.

FIG. 2(*a*) is a side view of the medical vehicle 200 according to some example embodiments as viewed from the Z-axis direction. The medical vehicle 100 includes a computed tomographic (CT) system, also referred to herein simply as a CT, shown in FIG. 2(*a*) as CT 63. Unlike some example embodiments, including the example embodiments shown in at least FIG. 1(*a*), the front side of the medical vehicle 200 faces rightward in FIG. 2(*a*). The medical vehicle 200 is equipped with a solar panel 71 to utilize natural energy like a solar power to serve as a power supply for the medical vehicle 200 (including at least the CT 63 included therein), and stairs 18 for entering and exiting the medical vehicle 200. There is a subject window 20 (e.g., first subject window) on the side face of the medical vehicle 200, and a bed 3-1 on which a subject such as a human body, animal body, or the like may be placed can be inserted directly along the upper part of the bed supporting member 3S inside the CT 63. As described below, a second subject window (e.g., subject window 20') is formed on the opposite side of the medical vehicle 200 from a first subject window (e.g., subject window 20). Accordingly, as shown, subject windows 20 and 20' are formed in surfaces and are configured to be exposed to the exterior of the medical vehicle 200 via opposite, respective left and right side faces such that the subject windows 20, 20' are configured to enable a subject to enter or exit from the inner peripheral of the CT gantry 5 in a body axis direction of the CT 63 in relation to the exterior of the medical vehicle via the left or right side face of the medical vehicle 200. In FIGS. 2(*a*)-2(*b*) the subject windows 20, 20' are formed in respective left and right side faces, but in some example embodiments the subject windows 20, 20' may be formed in separate, respective inner surfaces of a medical vehicle that are configured to be exposed to an exterior of the medical vehicle via separate, respective spaces (e.g., entrance spaces 57) between the respective inner surfaces, and separate (e.g., opposite left and right) side faces of the medical vehicle. In FIG. 2(*a*), the inner peripheral part of the gantry 5 is shown. The body axis direction of the gantry portion of the CT 63 is perpendicular to the X-Y plane. In some example embodiments, the central axis of the inner peripheral part of the gantry 5 corresponds to the central axis of the circular shaped subject window(s) 20, 20'. As shown, the respective central axes of the subject windows 20, 20' may be the same as a single, common, axis (e.g., the central axis of the subject window 20' may be coaxial with the central axis of the subject window 20).

FIG. 2(*b*) is a plan view of a main part of the medical vehicle 200 as viewed from the Y-axis direction. In some example embodiments, the subject windows 20, 20' are provided near the left and right side faces of the medical vehicle 200. The body axis direction of the CT 63 is oriented at right angles to (e.g., oriented perpendicular to) the straightforward direction (e.g., a direction of a longitudinal axis) of the medical vehicle 200, and the respective central axes of the right and left-side subject windows (e.g., subject windows 20 and 20') correspond to (e.g., are coaxial to and/or are the same as) the central axis of the inner peripheral of the CT gantry 5 in the body axis direction of the CT 63. A tubular shaped subject protector 51 is placed to penetrate the inner peripheral portion of the gantry 5 to prevent the subject from contacting with the gantry 5 as the subject moves along and/or in relation to the gantry 5, or reduce the likelihood of the subject contacting the gantry 5 as the subject moves along and/or in relation to the gantry 5. The diameter of each of the subject windows 20, 20' may be larger than the diameter of the inner peripheral of the subject protector 51, and the diameter of each of the subject windows 20, 20' may be smaller than the diameter of the outer diameter (e.g., outer peripheral) of the CT gantry 5. Further, funnel-shaped subject protectors 53 are attached between the subject protector 51 and the subject windows 20, 20' to prevent outside air from entering the inside of the medical vehicle 200, or reduce the likelihood of outside air entering the inside of the medical vehicle 200. The subject lying on the bed 3-1 is guided into the CT 63 by the bed supporting member 3-2. Stroke regions required by the CT 63 are not inside the medical vehicle 200, but are outside the medical vehicle 200. In some example embodiments, the gantry 5, which has a rotating part, is fixed to the central portion of the medical vehicle 200 in the Z-axis direction. The gantry 5 is fixed relation to the medical vehicle 200 and the imaging process is performed while the bed 3-1 on which the subject is placed is moving in relation to the medical vehicle 200.

Further, as shown in FIG. 2(*b*), a driver's seat 60 and a passenger's seat 70 are provided in front of the medical vehicle 200. The passenger's seat 70 can be rotated (e.g., reversed) to face a backward direction to face the CT 63 and to be used as a CT operator's seat. In some example embodiments, the backrest of the passenger's seat 70 may be reversed to become the CT operator's seat. Based on the CT operator using the passenger's seat when operating the CT 63, no additional space for the CT operator to operate the CT 63 to perform the CT operation is required inside the medical vehicle 200. As mentioned above, the driver's seat 60 and the steering wheel 80 are placed on the right side and the passenger's seat 70 is located on the left side of the medical vehicle 200. In some example embodiments, the passenger's seat 70 may be located on the right side when the driver's seat 60 and the steering wheel 80 may be placed on the left side of the medical vehicle 200.

The tomographic images reconstructed by the image drawing circuit (which may include, be included in, and/or be implemented by the control unit 22-1) and software are displayed on a display monitor 22-2. An operation and control part, also referred to herein interchangeably as a control unit 22-1, and a display monitor 22-2 are provided at the backside of the passenger's seat 70 which will become the CT operator's seat. The control unit 22-1 and the display monitor 22-2 are communicatively coupled to each other, such that the display monitor 22-2 is configured to display images based on signals generated at the control unit 22-1 and transmitted to the display monitor 22-2. The control unit 22-1 is communicatively coupled (also referred to herein as electrically coupled) to at least a data processing unit. A tomographic image reconstructed by an imaging circuit (which may include, be included in, and/or be implemented by the control unit 22-1) and software in the data processing unit (which may include, be included in, and/or be implemented by the control unit 22-1) in response to an imaging operation being performed by some or all of the CT 63 may be displayed on the display monitor 22-2. The medical vehicle 200 may include some separate rooms such as a data processing and a power supply room 16-1 which may include the above-mentioned data processing unit, other testing equipment room 16-2, a biochemical analyzing room 16-3, a consultation room 16-4, a waiting room 16-5, a dressing room 16-6), and a cabin passage 16P, for example. The doors 52-1 and 52-2 are provided to shut the CT 63 from the outside of the vehicle when the CT 63 is not used or the medical vehicle 200 is moving. With this configuration, the subject can be carried in or out from either the left or right side of the medical vehicle 200.

FIG. 2(*c*) is a cross-sectional view of a main part of the medical vehicle 210 which includes a computed tomographic (CT) system, also referred to herein simply as a CT, shown in FIG. 2(*c*) as CT 63, particularly when the CT 63 is viewed from the rear of the medical vehicle 210 in the X-axis direction. The bed 3-1 on which the subject is placed passes through the gantry 5 of the CT 63 from one of the subject windows 20, 20' and exits through the other side of the medical vehicle 210 via the other one of the subject windows 20, 20' by the movable bed supporting members 3-2. As explained above, the diameter of each of the subject windows 20, 20' may be larger than the diameter of the inner peripheral of the subject protector 51, and the diameter of each of the subject windows 20, 20' may be smaller than the diameter of the outer diameter (e.g., outer peripheral) of the CT gantry 5. A rotatable light source is placed inside the gantry 5 and takes a tomographic image of the subject while the bed 3-1 is moving in the Z-axis direction. In some example embodiments, the gantry 5 is fixed to the floor surface (e.g., vehicle floor 55-1), and a subject protector 51 is attached to penetrate the inner peripheral portion of the gantry 5. A funnel-shaped subject protector 53 continuously connects the side face of the medical vehicle 210 and the subject protector 51. With this configuration, the inside of the medical vehicle 210 can be shielded from the external environment, so that the temperature or humidity fluctuation inside the medical vehicle, especially the characteristic fluctuation of the CT 63 such as the sensitivity fluctuation of the detector due to the temperature or humidity dependence of the scintillator can be suppressed. In addition, it makes possible to prevent droplets emitted from the nose or the mouth of the subject or outside dust from entering the medical vehicle, or reduce the likelihood of droplets emitted from the nose or the mouth of the subject or outside dust entering the medical vehicle. As shown in FIG. 2(*c*), the bed supporting member 3-2 can be arranged at the left and the right-side surfaces of the medical vehicle 210. The subject can be carried in from one of the subject windows 20, 20' and can be carried out from the opposite side of the medical vehicle 210 via the other one of the subject windows 20, 20'. In this way, it is suitable for many subjects to be examined continuously, for example. Conventionally, it was necessary to secure almost double the stroke area inside the vehicle corresponding to the carry-in side and the carry-out side. With this configuration, many subjects can be efficiently tested without requiring such a stroke area or a large waiting room inside the medical vehicle 210.

Figures 3A, 3B, 3C, 3D:
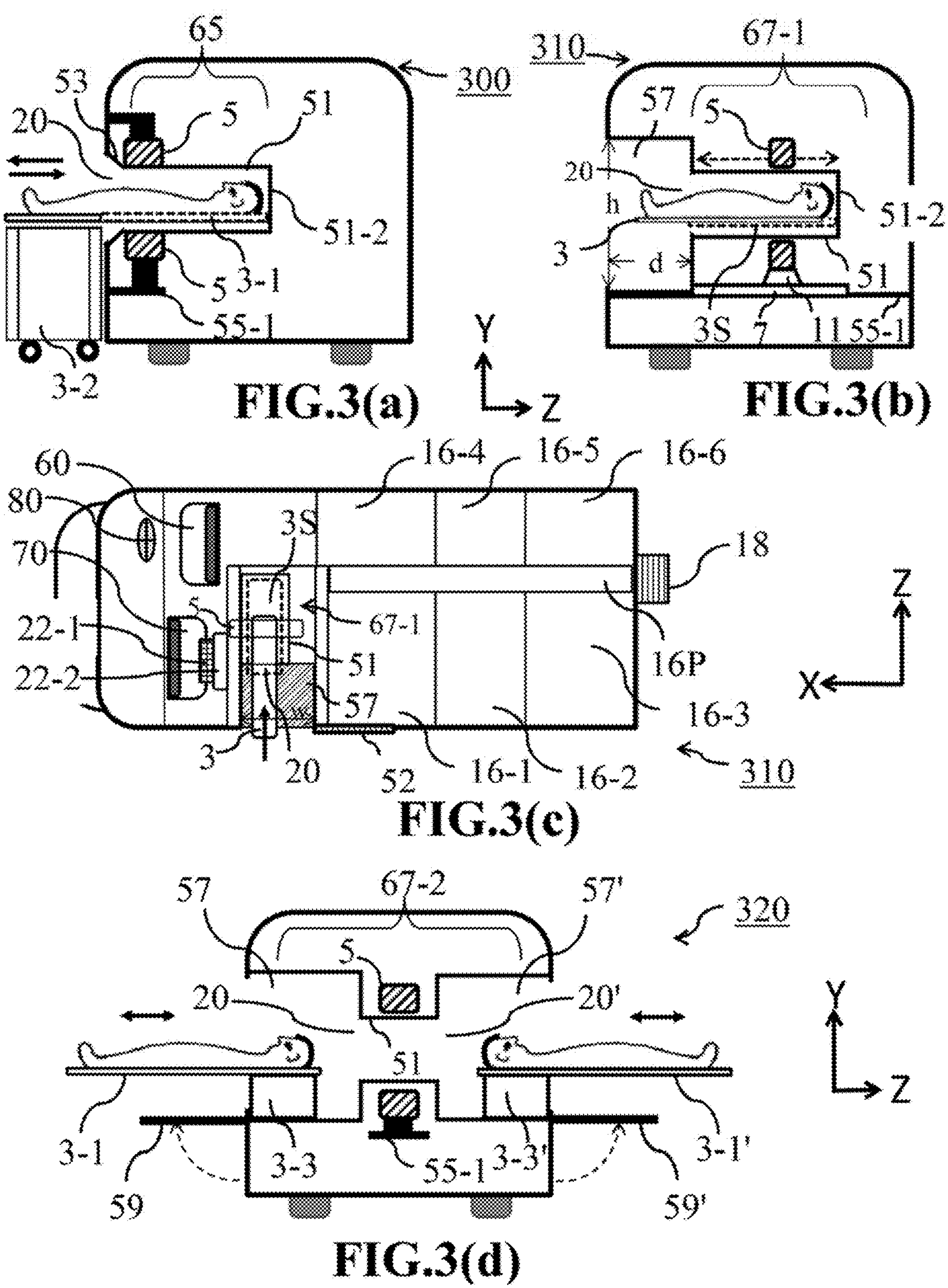
FIG. 3(*a*) is a cross-sectional view of a medical vehicle, particularly illustrating an arrangement of a CT of the medical vehicle viewed from a rear portion (X-axis direction), according to some example embodiments.

With reference to FIGS. 3(*a*)-3(*d*), the medical vehicle 300, 310, and 320 according to some example embodiments will be described below.

FIG. 3(*a*) is a cross-sectional view of a main part of the medical vehicle 300 according to some example embodiments as viewed from the rear side of X-axis direction. The medical vehicle 300 includes a computed tomographic (CT) system, also referred to herein simply as a CT, shown in FIG. 3(*a*) as CT 65. As shown in FIG. 3(*a*), there is a subject window 20 for loading or unloading the subject into or from the CT 65 at the one side face of the medical vehicle 300, and a funnel-shaped subject protector 53 and a subject protector 51 are continuously formed from the side face of the medical vehicle 300. Further, the end portion 51-2 of the subject protector 51 is formed at the other end of the subject protector 51, which has a closed shape to shut against the inside of the medical vehicle 300. Therefore, the inside (e.g., the interior) of the medical vehicle 300 is separated from the external environment (e.g., exterior) of the medical vehicle 300, which is also described as an ambient environment. The characteristic fluctuations of the CT 65 in temperature and humidity inside the medical vehicle 300 can be suppressed, and droplets emitted from the nose or the mouth of the subject or outside dust can be prevented from entering the medical vehicle 300, or the likelihood of droplets emitted from the nose or the mouth of the subject or outside dust entering the medical vehicle 300 may be reduced. The end portion 51-2 of the subject protector 51 that is the opposite side of the subject window 20 may be either closed or open against the inside of the medical vehicle 300 by an openable door because the subject's feeling of blockage or oppression may be reduced by opening the door in the case of no concern about temperature or humidity fluctuations or droplet infection from the subject. In some example embodiments, the gantry 5 of the CT 65 is fixed (e.g., fixed in relation to the medical vehicle 300) in the vicinity of the subject window 20 (e.g., near the side face through which the subject window 20 may be exposed to the exterior of the medical vehicle 300) on the vehicle floor 55-1, and the subject lying on a movable bed 3-1 is carried into the CT 65 by a movable bed supporting member 3-2. Therefore, the stroke area required by the CT 65 is not inside the medical vehicle 300 but outside the medical vehicle 300. Further, the space inside the medical vehicle 300 can be used more effectively since the space occupied by the gantry 5 is fixed and limited in the vicinity of the subject window 20. As described above, if the dimension of the CT 65 in the Z-axis direction is, for example, a length sufficient for photographing the upper body of the subject, the space occupied by the CT 65 in the medical vehicle 300 can be reduced even further.

FIG. 3(*b*) is a cross-sectional view of a main part of the medical vehicle 310 as viewed from the rear side of X-axis direction. The medical vehicle 310 includes a computed tomographic (CT) system, also referred to herein simply as a CT, shown in FIG. 3(*b*) as CT 67-1. A subject window 20 is formed on one side face of the medical vehicle 310. The opening area of the subject window 20 is larger than the opening area of the subject protector 51 as viewed from X-axis direction. Further, an entrance space 57 is formed toward the inside of the medical vehicle 310 as shown by the height h and the depth d. Restated, and as shown in at least FIG. 3(*b*), the subject window 20 may be formed in an inner surface within an interior of the medical vehicle 310 and spaced inward into the interior from a side face by depth d, the side face of the medical vehicle 310 may include a further opening having at least height h, and one or more inner surfaces of the medical vehicle 310 (including the surface in which the subject window 20 is formed) may at least partially define an entrance space 57 between the subject window 20 and the side face of the medical vehicle 310 and having height h and depth d within the interior of the medical vehicle 310, such that the subject window 20 is configured to be exposed to the exterior of the medical vehicle through the side face via at least the entrance space 57 as shown in at least FIG. 3(*b*). The height h and depth d of the entrance space 57 may allow a subject (e.g., person, human body, animal body, or the like) to sit on or lie down on the bed 3 personally and may play the role of a small front chamber. As described in FIG. 3(*a*), the end portion 51-2 of the subject protector 51, that is the opposite side of the subject window 20 may be either closed or open against the inside of the medical vehicle 310 by an openable door. The gantry 5 moves on the gantry table 7 (e.g., moves in relation to the gantry table 7 and thus moves in relation to the medical vehicle 310, portions of the CT 67-1, etc.). A gantry moving carriage 11 may be attached to the gantry 5. The gantry table 7 is attached on the vehicle floor 55-1. The CT 67-1 has a structure in which a subject lies on the bed 3 and is slid on the bed supporting member 3S until stopped. The gantry 5 may take (e.g., capture, generate, etc.) an image while the gantry 5 is moving in the Z-axis direction. The moving distance of the gantry 5 in the Z-axis direction may be the length of the upper body, about 1 meter, for example.

FIG. 3(*c*) is a plan view of a main part of the medical vehicle 310 as viewed from the Y-axis direction. The width w of the entrance space 57 shown by the shaded area allows the subject can easily get on the bed 3, may be about 1 m, for example. In some example embodiments, the wall surface of the entrance space 57 is formed integrally with the subject protector 51 to prevent outside air from entering the inside of the medical vehicle 310, or reduce the likelihood of outside air entering the inside of the medical vehicle 310. With this configuration, characteristic fluctuations of the CT 67-1 in temperature and humidity inside the vehicle can be suppressed, reduce the likelihood of droplets emitted from the nose or mouth of the subject and outside dust entering the vehicle, or prevent droplets emitted from the nose or mouth of the subject and outside dust from entering the medical vehicle 310. Like some example embodiments, including the example embodiments of the medical vehicles 100, 200, and 210 as shown in FIGS. 1(*a*) to 2(*c*), the tomographic images reconstructed by the image drawing circuit and software are displayed on the monitor. Further, as shown in FIG. 3(*c*), a driver's seat 60 and a passenger's seat 70 are provided in front of the medical vehicle 310. The passenger's seat 70 can be rotated (e.g., reversed) to face a backward direction to face the CT 61 and to be used as a CT operator's seat. In some example embodiments, the backrest of the passenger's seat 70 may be reversed to become the CT operator's seat. Based on the CT operator using the passenger's seat when operating the CT 67-1, no additional space for the CT operator to operate the CT 67-1 to perform the CT operation is required inside the medical vehicle 310. As mentioned above, the driver's seat 60 and the steering wheel 80 are placed on the right side and the passenger's seat 70 is located on the left side of the medical vehicle 310. In some example embodiments, the passenger's seat 70 may be located on the right side when the driver's seat 60 and the steering wheel 80 may be placed on the left side of the medical vehicle 310. An operation and control part, also referred to a control unit 22-1, and a display monitor 22-2 are provided at the backside of the passenger's seat 70 which will become the CT operator's seat. The control unit 22-1 and the display monitor 22-2 are communicatively coupled to each other, such that the display monitor 22-2 is configured to display images based on signals generated at the control unit 22-1 and transmitted to the display monitor 22-2. The control unit 22-1 is communicatively coupled (also referred to herein as electrically coupled) to at least a data processing unit. A tomographic image reconstructed by an imaging circuit and software in the data processing unit in response to an imaging operation being performed by some or all of the CT 67-1 may be displayed on the display monitor 22-2. Further, as already mentioned above, the medical vehicle 310 may include some separate rooms such as a data processing and a power supply room 16-1 which may include the above-mentioned data processing unit, other testing equipment room 16-2, a biochemical analyzing room 16-3, a consultation room 16-4, a waiting room 16-5, a dressing room 16-6, and a cabin passage 16P, for example. The door 52 is provided to shut the CT 67-1 from the outside of the vehicle when the CT 67-1 is not used or the medical vehicle 310 is moving. With this configuration, the moving distance of the gantry 5 in the Z-axis direction may be the length of the upper body, about 1 meter, for example. The stroke region required by the CT 67-1 is outside the medical vehicle 310, and subjects can ride or lie down on the bed inside the CT 67-1 by themselves without using a subject moving means such as a stretcher. This structure may be also useful in case of rainy weather, for example.

FIG. 3(*d*) is a cross-sectional view of a main part of the medical vehicle 320 as viewed from the rear side of X-axis direction according to the some example embodiments. The medical vehicle 320 includes a computed tomographic (CT) system, also referred to herein simply as a CT, shown in FIG. 3(*d*) as CT 67-2. As shown in FIG. 3(*d*), the subject windows 20, 20' are provided on both (e.g., opposite) left and right-hand sides of the medical vehicle 320. Like the medical vehicle 310 described above, the opening (e.g., diameter of each of the subject windows 20, 20') seen from the X-axis direction is larger than the opening of the subject protector 51 and having right and left entrance spaces 57, 57' extending toward the inside of the medical vehicle 320. The height, width, depth of the entrance spaces 57, 57' may enable a subject (person, human body, animal body, etc.) to sit on or lie down on one of the beds 3-1, 3-1' personally. In some example embodiments, in some example embodiments, the gantry 5 is located at the center of the medical vehicle 320 in the body axis direction of the CT 67-2, or the Z-axis direction (e.g., is equidistantly or substantially equidistantly between the left and right side faces of the medical vehicle 320 in the body axis direction of the CT 67-2 as shown) and is fixed to the vehicle floor 55-1 of the medical vehicle 320. The length of the subject protector 51 in the Z-axis direction can be shortened. Two entrance spaces 57, 57' can be provided, where each entrance space 57, 57' is at least partially defined by one or more inner surfaces of the medical vehicle 320 and is between a separate one of the subject windows 20, 20' and a separate side face of the medical vehicle 320. Further, as shown in FIG. 3(*d*), auxiliary plates 59, 59' may be attached to the body of the medical vehicle 320 on either or both of the opposite side faces and of the medical vehicle 320 and each may be rotated by 90 degrees when it is used to expand the stroke region outside the medical vehicle 320. In some example embodiments, the subject, lying on one of the beds 3-1, 3-1' of the bed moving device, is transported into the CT 67-2 by a respective one of the small subject conveying devices 3-3, 3-3'. With this structure, CT examination can be performed from either the left or the right side of the medical vehicle 320, and stroke area can be reduced using one or more of the auxiliary plates 59, 59'. Like the medical vehicle 210, it becomes possible to perform efficient CT examinations on a lot of subjects continuously or serially moving the subjects in one direction or bidirectionally. Further, fluctuations of the CT 67-2 characteristics on temperature and humidity inside the vehicle can be suppressed, and droplets emitted from the nose or mouth of the subject and dust from outside the vehicle can be reduced or prevented since the internal environment of the medical vehicle 320 is shielded from the external environment of the medical vehicle 320.

Figure 4C:
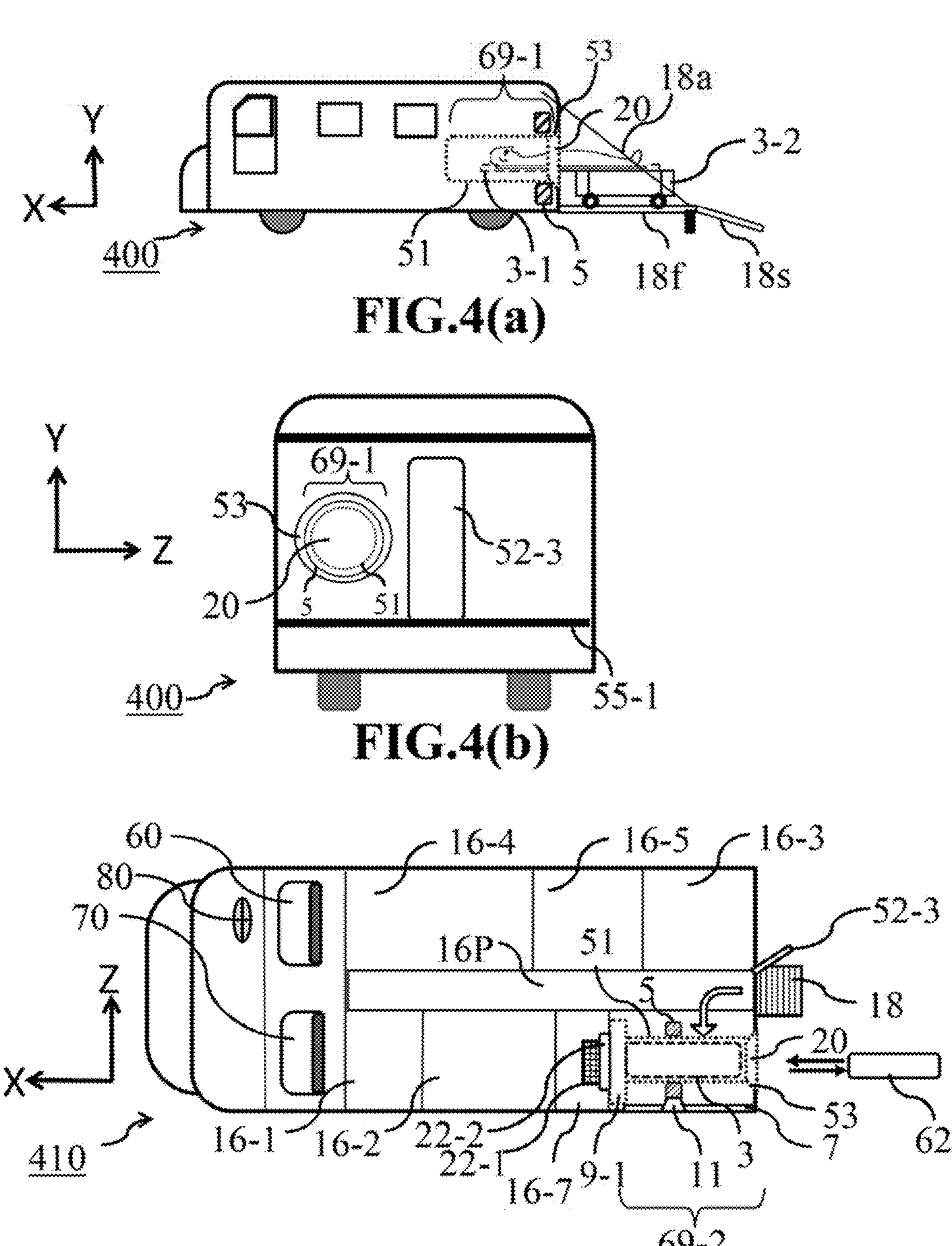
FIG. 4(*a*) is a side view of a medical vehicle viewed from a Z-axis direction, according to some example embodiments.

With reference to FIGS. 4(*a*)-4(*c*), the medical vehicles of 400 and 410 according to some example embodiments will be described below.

FIG. 4(*a*) is a side view of a main part of the medical vehicle 400 as viewed from the Z-axis direction. The medical vehicle 400 includes a computed tomographic (CT) system, also referred to herein simply as a CT, shown in FIG. 4(*a*) as CT 69-1. A subject window 20 is provided at the rear side face of the medical vehicle 400. Restated, the side face of the medical vehicle 400 through which the subject window 20 may be exposed to the exterior of the medical vehicle 400 may be a rear side face of the medical vehicle. The CT 69-1 is arranged in the vehicle so that the body axis direction of the gantry 5 coincides with the X-axis direction (e.g., the body axis direction of the CT 69-1, the gantry 5, or the like is parallel to and/or paraxial to the direction of the longitudinal axis of the medical vehicle 400). The outside air is reduced or prevented from easily entering the medical vehicle 400 by the subject protector 51 and the funnel-shaped subject protector 53. The inside of the medical vehicle 400 can be shielded from the external environment of the medical vehicle 400, so that the characteristic fluctuations of the CT 69-1 like temperature and humidity dependencies inside the medical vehicle 400 can be suppressed, or droplets emitted from the nose or mouth of the subject and dust entering the medical vehicle 400 can be reduced or prevented. The bed 3-1 on which the subject such as a human body, animal body, or the like is laid can be inserted into the CT 69-1 by the moving bed supporting member 3-2. In the meantime, the gantry 5 attached near the side face of the rear part of the medical vehicle 400 will carry out imaging. As shown in FIG. 4(*a*), an auxiliary plate **18*f* is attached to the vehicle body of the medical vehicle 400 to fit the height of the CT 69-1 by rotating 90 degrees in relation to the medical vehicle 400 using a wire 18*a* to create a horizontal stroke region. The moving bed supporting member 3-2 can be moved onto the slope 18**S.

FIG. 4(*b*) is a plan view of the rear portion of the medical vehicle 400 as viewed from the X-axis direction. A funnel-shaped subject protector 53 is attached to the subject protector 51 to define the subject window 20. In some example embodiments, the central axis of the inner peripheral part of the gantry 5 corresponds to the central axes of the circular shaped subject window 20 and the circular shaped subject protector 51. The medical vehicle 400 has an openable door 52-3 on the vehicle floor 55-1 for a subject to enter the medical vehicle 400. In this way, the space inside the medical vehicle 400 can be effectively utilized without increasing the size of the medical vehicle 400 since the stroke region required by the CT 69-1 is not inside the medical vehicle 400 but behind and outside the medical vehicle 400. The stroke area can be easily secured outside the medical vehicle 400 even in a narrow place or a passage.

FIG. 4(*c*) is a plan view of a main part of the medical vehicle 410 as viewed from the Y-axis direction according to some example embodiments, including a modified example embodiment of the medical vehicle 400. The medical vehicle 410 includes a computed tomographic (CT) system, also referred to herein simply as a CT, shown in FIG. 4(*c*) as CT 69-2. As shown in FIG. 4(*c*), a driver's seat 60 and a passenger's seat 70 are provided in front of the medical vehicle 410. The gantry 5 has a rotatable light source (e.g., X-ray generator) inside the gantry 5 and takes a tomographic image of the subject while moving in the X-axis direction in relation to the medical vehicle 410. The gantry 5 moves along the subject (e.g., moves in relation to the medical vehicle 410, portions of the CT 69-2 such as the gantry table 7, etc.). A subject protector 51 is placed to penetrate the inner peripheral portion of the gantry 5. The gantry 5 moves above the gantry table 7. A gantry moving carriage 11 is attached to the gantry 5. As shown in FIG. 1(*d*), the gantry table 7 of the medical vehicle 410 may be attached to the side face of the medical vehicle 410. Further, as described later, the cradle 9-1 is attached on the opposite side of the subject window 20 at the other end of the moving range of the gantry 5 so as to close the other side of the opening of the subject protector 51. The cradle 9-1 may perform electrical and/or mechanical coupling with the gantry 5. The medical vehicle 410 may include some separate rooms such as a data processing and a power supply room 16-1, other testing equipment room 16-2, a biochemical analyzing room 16-3, a consultation room 16-4, a waiting room 16-5, a dressing room 16-6, a CT operator's room 16-7, and a cabin passage 16P, for example. An operation and control part, also referred to a control unit 22-1, and a display monitor 22-2 are provided in the CT operator's room 16-7. The control unit 22-1 and the display monitor 22-2 are communicatively coupled to each other, such that the display monitor 22-2 is configured to display images based on signals generated at the control unit 22-1 and transmitted to the display monitor 22-2. The control unit 22-1 is communicatively coupled (also referred to herein as electrically coupled) to at least a data processing unit. A tomographic image reconstructed by an imaging circuit and software in the data processing unit in response to an imaging operation being performed by some or all of the CT 69-2 may be displayed on the display monitor 22-2. In some example embodiments, the gantry 5 takes an image while the gantry 5 moves in the body axis of the X-axis direction with respect to the subject. A subject can be introduced from the outside of the medical vehicle 410 with the aid of a stretcher 62, for example. In the medical vehicle 410, the CT 69-2 can be used even when the subject window 20 is shielded because the side surface of the subject protector 51 can be either openable or closable with respect to the side of the cabin passage 16P. Subjects or patients can ride on the bed 3 from the vehicle interior side and lie on the bed 3 as shown by a void arrow mark. With this structure, inspections can be conducted without the influence of the outside air and infection from the patient by guiding the subject from outside the medical vehicle 410 with the aid of a stretcher 62. In addition, subjects may walk into the medical vehicle 410 and have inspections if there are no such concerns. The structure may be also useful in rainy weather, for example. The entrance space 57 described with reference to FIG. 3(*b*) can be also provided in the medical vehicles 400 and 410 accordingly.

Figures 5A, 5B, 5C:
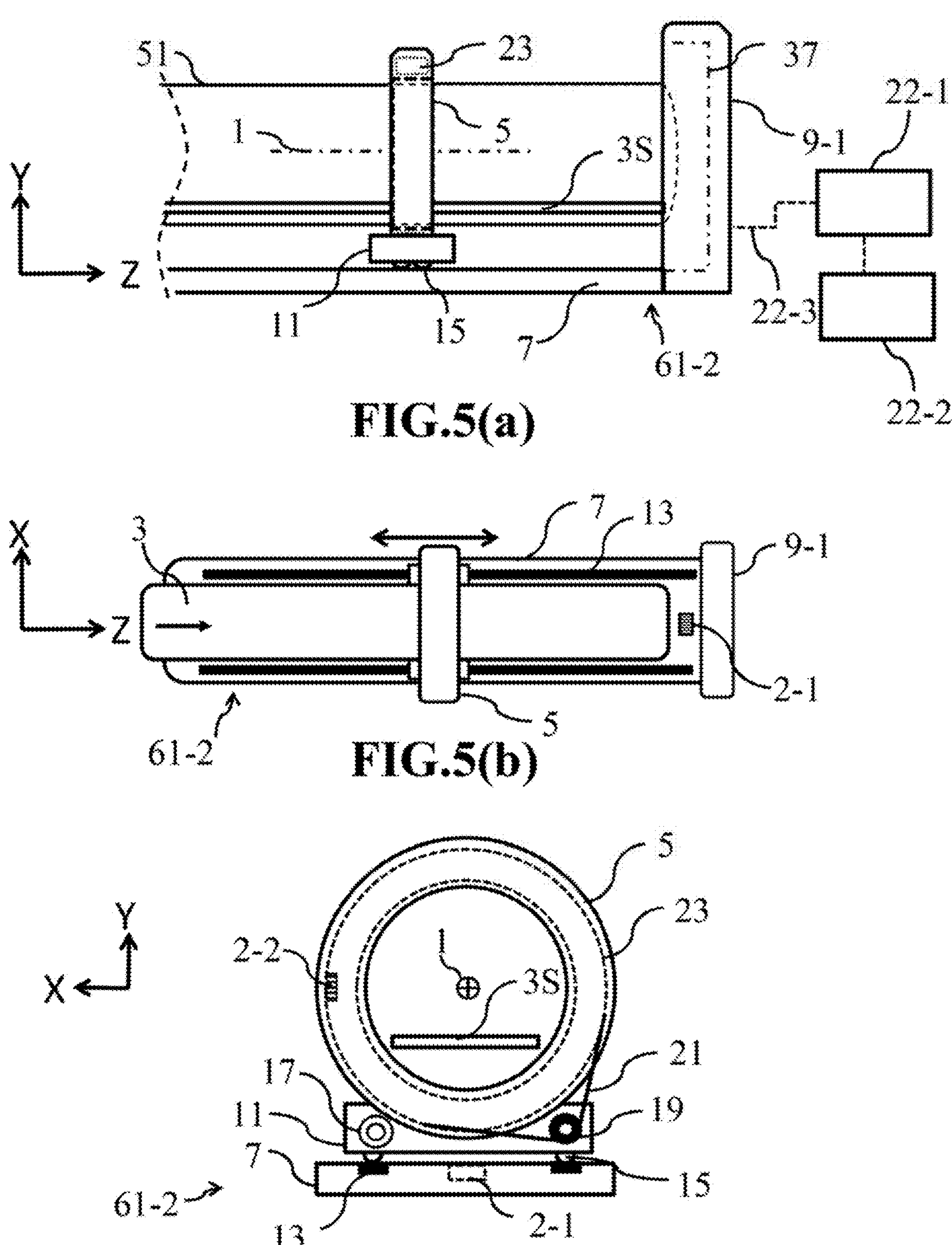
FIG. 5(*a*) is a side view of a CT viewed from an X-axis direction, according to some example embodiments.

The CT structure of a CT suitable for some example embodiments like the CTs of any of the medical vehicles 100 in FIGS. 1(*a*)-1(*d*) will be described below. With reference to FIGS. 5(*a*)-5(*c*), the CT 61-2 having a gantry 5 on the gantry table 7 is discussed in detail. It will be understood that any of the CTs according to some example embodiments, including any of CT 61, CT 67-1, and/or CT 69-2, may include the same structure as CT 61-2 as shown in FIGS. 5(*a*)-5(*c*) and/or may include at least some of the elements of CT 61-2 as shown in FIGS. 5(*a*)-5(*c*).

FIG. 5(*a*) is a side view of a main part of CT 61-2 as viewed from the X-axis direction. The CT 61-2 comprises a gantry table 7, a cradle 9-1, and a movable gantry carriage 11 having wheels 15 to facilitate the movement in the Z-axis direction. The gantry 5 can be retracted and fixed in the gantry storage portion 37 as shown by the broken line when CT imaging is not performed. The gantry 5 can be protected from vibration or the like while the medical vehicle in which the CT 61-2 is located is moving. In some example embodiments, a cylindrical (e.g., tubular shaped) subject protector 51 is arranged inside the gantry 5. Further, the CT 61-2 may have a bed supporting member 3S which guides and holds the subject being placed on a bed 3. Inside the gantry 5, a rotatable rotating part having its rotational central axis 1 is provided. It should be noted that there is an operation or control unit 22-1, and a display monitor 22-2. A tomographic image reconstructed by an image drawing circuit and software can be displayed on the monitor (e.g., display monitor 22-2). During the imaging, only the gantry 5 moves in the Z-axis direction, and the subject is stationary on the bed 3. Therefore, in this structure, a robust and precise subject movement control means is not required, and the CT 61-2 itself can be made smaller and lighter. Further, in the case when the scanning speed in the body axis (Z axis) direction of the gantry is increased, the physical and mental load or anxiety of the subject will be reduced. The gantry 5 may be towed or pushed from the cradle 9-1 side to move the gantry 5 in the Z-axis direction.

FIG. 5(*b*) is a plan view of a main part of CT 61-2 as viewed from the Y-axis direction. Two rails 13 are provided on the upper part of the gantry table 7 on which the gantry 5 may move. Using a conductive material such as metal for the rail 13 and the wheels 15, electrical power can be supplied to the drive motor 17 inside the movable gantry carriage 11, or a control signal can be sent to and from the movable gantry carriage 11. The host interface 2-1 which is an electrical connection means for exchanging electric signals or electric power between the rotating part 23 and the gantry table 7 is set on the upper part of the gantry table within the movement range of the gantry 5 or may be arranged at the end point of the movement range of the gantry 5. The gantry 5 can be taken away from the gantry table 7 by removing the bed supporting member 3S. Then, it becomes easy to maintain, or replace the gantry 5 with a new one showing different imaging characteristics, such as a light source (e.g., X-ray generator) inside the gantry 5 having a different light energy or wavelength, for example.

FIG. 5(*c*) is a plan view of a main part of CT 61-2 as viewed from the Z-axis direction. A rotating part 23 inside the gantry 5 rotates around the rotating center 1 is attached via ball bearings (not shown in FIG. 5(*c*)), for example. A timing belt 21 for rotating the rotating part 23 is attached to the gantry rotating part drive motor 19 inside the movable gantry carriage 11. The rotating part 23 has the rotating part interface 2-2, then the rotating part 23 can be electrically connected at a position facing the host interface 2-1 when the rotating part 23 is stationary. In some example embodiments, a position sensor (not shown in FIG. 5(*c*)) using a Hall element or the like is used so that the rotating part interface 2-2 will stop at the position to face the host interface 2-1. Further, a gantry moving carriage drive motor 17 for moving the gantry 5 in the Z-axis direction is provided inside the gantry moving carriage 11. The electrical power for driving the carriage can be supplied from the rail 13 for the gantry carriage as described above, or a rechargeable battery can also be built in the gantry moving carriage 11. As will be described below, the host interface may be located at the cradle 9-1 and can be electrically connected with the rotating part interface of the gantry 5 by approaching or being coupled to the cradle 9-1.

Contactless power supply and an electrical signal transfer between the host interface of the cradle side and the rotating part interface of the gantry side will be described with reference to FIG. 6 (*a*) and FIG. 6 (*b*).

Figures 6A, 6B:
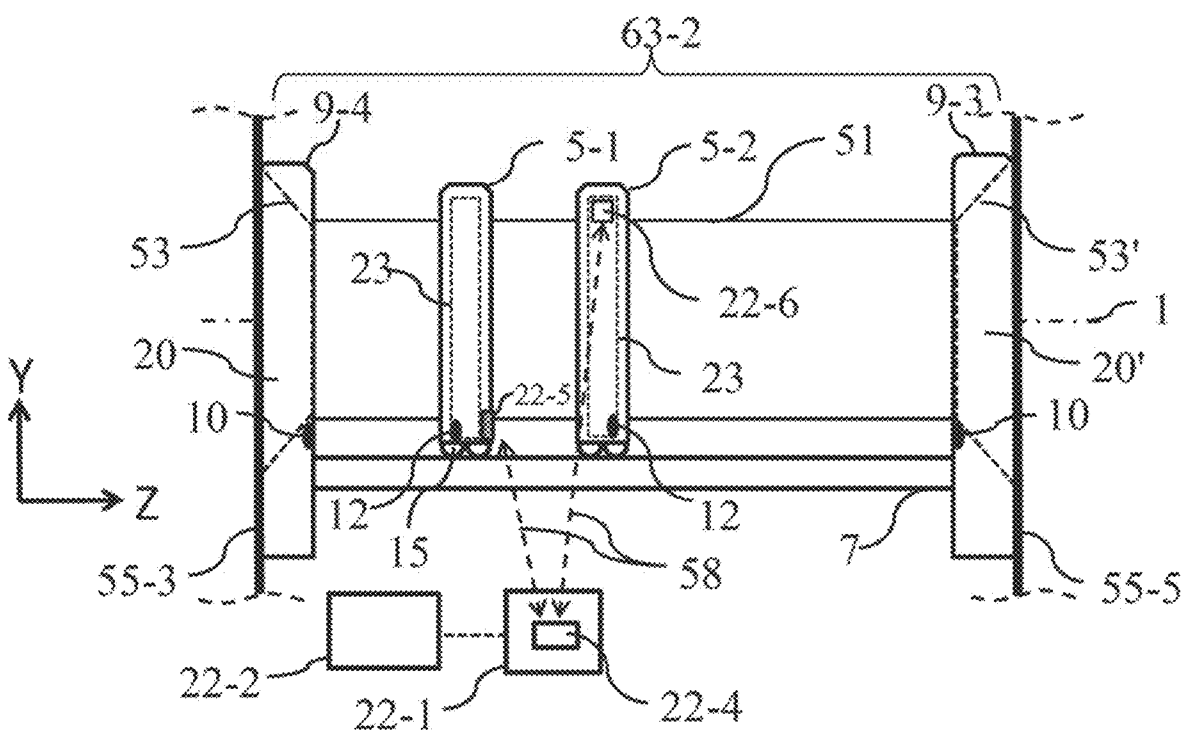
FIG. 6(*a*) is a side view of a CT viewed from an X-axis direction, according to some example embodiments.

FIG. 6(*a*) shows a CT (63-2) in which the gantry 5 moves in the body axis direction with respect to the stationary subject as described in the case of the medical vehicle 100. It will be understood that any of the CTs according to some example embodiments, including any of CT 61, CT 67-1, and/or CT 69-2, may include the same structure as CT 63-2 and/or may include at least some of the elements of CT 63-2 as shown in FIG. 6(*a*). There are two subject windows 20, 20' on both the left and right sides (55-3, 55-5) (e.g., the two subject windows 20, 20' may be at separate, respective opposite sides 55-3 and 55-5) of the vehicle. Further, the cradles 9-3 and 9-4 are provided in the vicinity of the left and right subject windows 20, 20'. Therefore, each gantry 5-1, 5-2 can be electrically coupled to either the left or the right cradles, respectively. In some example embodiments, two gantries 5-1 and 5-2 are provided in the CT 63-2. Funnel shape subject protectors 53, 53' are attached continuously to the subject protector 51. The subject protector 51 penetrates inside of the cradle 9-3 and 9-4 in the Z-axis direction. The left and right cradles 9-3 and 9-4 have contactless host interfaces 10, and the gantries 5-1 and 5-2 each have a contactless rotating part interfaces 12 where the gantry 5-1, 5-2 can be close to the rotating part face to face. As described above, a position sensor using a Hall element sensor may be used to stop the rotating unit interface 12 to face the host interface 10.

The cradle 9-3 and 9-4 have donut-shaped hollows (e.g., may be donut-shaped or torus-shaped to have a central opening) so that a subject and a bed (not shown in FIG. 6(*a*)) can pass through the hollows (e.g., central opening). Further, a subject protector 51 is provided above the gantry table 7 along the moving direction of the gantry 5-1, 5-2 in order to prevent the subject or the object to be examined from coming into contact with the gantry during the movement of the gantry 5-1, 5-2, or reduce the likelihood of the subject or the object to be examined coming into contact with the gantry 5-1, 5-2 during the movement of the gantry in relation to the subject or object to be examined. The CT 63-2 enables various examinations by the multiple gantries such as a combination of X-ray CT inspection gantry and PET (positron emission tomography) inspection gantry, or combination of X-ray CT inspection gantry and near infrared diffused light imaging gantry. The plurality of gantries 5-1, 5-2 can be driven individually or in conjunction with each other. In some example embodiments, a high-speed wireless communication interface may be introduced between the gantry (e.g., wireless communication interface 22-5) or the rotating part (e.g., wireless communication interface 22-6) and the operational control part (e.g., control unit 22-1, wireless communication interface 22-4), in order to monitor output signal like a fluoroscopic image of the subject from the rotating part or the gantry while the gantry 5-1, or 5-2 is moving in the body axis direction.

The control unit 22-1 may include a wireless communication interface 22-4 (e.g., a 5G wireless network communication transceiver, an ad hoc wireless network communication transceiver such as a Bluetooth® transceiver, or the like), and the gantry 5-1, 5-2 and/or a rotating part 23 of one or more of the gantries 5-1, 5-2 may include a corresponding wireless communication interface 22-6, 22-5, etc. (e.g., each of the wireless communication interfaces may be a 5G wireless network communication transceiver, an ad hoc wireless network communication transceiver such as a Bluetooth® transceiver, or the like) As shown in FIG. 6(*a*), the wireless communication interface 22-4 may establish one or more wireless communication links 58 with the corresponding wireless communication interfaces 22-5, 22-6, etc. to thus establish a wireless communication link(s) between the control unit 22-1 and one or more gantries 5-1, 5-2 and/or one or more rotating parts 23 of the CT system of the CT 63-2. Data, including image data generated at a rotating part 23 and/or one or more of the gantries 5-1, 5-2, may be transmitted to the control unit 22-1 via one or more wireless communication links 58. Control signals may be generated at the control unit 22-1 and transmitted to one or more of the gantries 5-1, 5-2 and/or rotating part 23 thereof via one or more of the wireless communication links 58. Such control signals may include control signals to cause one or more of the gantries 5-1, 5-2 and/or rotating part 23 thereof to engage in movement, control signals to cause one or more of the gantries 5-1, 5-2 to perform an imaging operation, some combination thereof, or the like. Therefore, in some example embodiments, the control unit 22-1 and at least one gantry 5-1, 5-2 have respective wireless communication interfaces 22-4, 22-5, 22-6, etc. configured to enable, by wireless communication between the control unit 22-1 and the gantry/gantries 5-1, 5-2, at least one of: transmitting and receiving a control signal to control movement of one or more of the gantries 5-1, 5-2 in the Z-axis direction by wireless communication, or causing one or more of the gantries 5-1, 5-2 to perform an imaging operation. With the CT 63-2 having two gantries 5-1 and 5-2, multi-image diagnosis using different light source energies (wavelengths or tube voltages, for example) will be realized for different medical fields such as orthopedics, cardiology, and gastroenterology, for example. Further, in addition to the X-ray CT, other types of gantries like a PET gantry or a gantry using near-infrared light source can be mounted on the gantry table 7 accordingly without introducing the second or the third separate medical imaging systems.

FIG. 6(*b*) is a block diagram related to electromagnetic induction type wireless power feeding circuits and wireless communication circuits with respect to the non-contact interface section (non-contact interfaces 10 and 12). It will be understood that any of the non-contact interfaces 10 and 12 of any CTs according to any of the example embodiments, may include the same structure as the non-contact interfaces 10 and 12 as shown in FIG. 6(*b*). It will be understood that CTs according to any of the example embodiments, including any of CT 61, CT 61-2, CT 63, CT 63-2, CT 65, CT 67-1, CT 67-2, CT 69-1, and/or CT 69-2, may include non-contact interfaces 10 and 12 as described herein according to any of the example embodiments, and such non-contact interfaces 10 and 12 may include the same structure as the non-contact interfaces 10 and 12 as shown in FIG. 6(*b*). As shown in FIG. 6(*b*), the circuit configuration on the contactless host interface side (10) includes an AC to DC converter (10-3) that converts a commercial power supply (10-2) (e.g., an external alternating current (AC) power supply network to which the gantry table 7 is communicatively coupled) into a direct current (DC), and a high frequency inverter (10-4) which outputs a high frequency square waveform. A waveform shaping circuit (10-5) converting the square waveform into a sine waveform is connected to the primary winding coil L1 (10-1) via an insulated transformer (10-6) for ensuring safety. In some example embodiments, the secondary winding coil L2 (12-1) is connected to a load such as a rechargeable battery (12-2), via a rectifying and waveform smoothing circuit (12-4) converting the high frequency current to a direct current followed by a reverse current blocking diode (12-3), for example. The contactless interfaces 10 and 12 may be configured to be electrically connected in a contactless manner based on an interaction of an electromagnetic field therebetween, based at least on the gantry 5 being at the particular (or, alternatively, predetermined) position such that the interfaces 10 and 12 are face to face with each other, such that a distance between the interfaces 10 and 12 is reduced or minimized such that interaction of an electromagnetic field between windings coils L1 and L2 (10-1) and (10-2) is enabled.

As for the transmitting and receiving control signals or image data, a wireless communication system based on near-field magnetic coupling for example, may be used. As shown in FIG. 6(*b*), antennas A1 and A2 closely face each other between non-contact interfaces 10 and 12, respectively. As shown in FIG. 6(*b*), these antennas A1 and A2 are connected to respective signal receivers (10-9, 12-9), also referred to herein as signal receiver circuits, and respective signal transmitters (10-8, 12-8), also referred to herein as signal transmitter circuits, which are configured to be controlled by respective controller circuits (10-7, 12-7). A spiral coil or a coupling capacitor electrode may be used as the near-field antenna (e.g., antennas A1 and A2), for example. As shown in FIGS. 6(*a*) and 6(*b*), it may be also preferable to introduce a high-speed and large-capacity communication method such as so-called 5G, for example, enabling a high-speed and a large-capacity CT image data transmission owing to the increased data transfer speed of giga (G) bits per second or more. Further, the wireless power feeding and the wireless communication system may be performed by sharing the same coil or antenna.

Figures 7A, 7B, 7C:
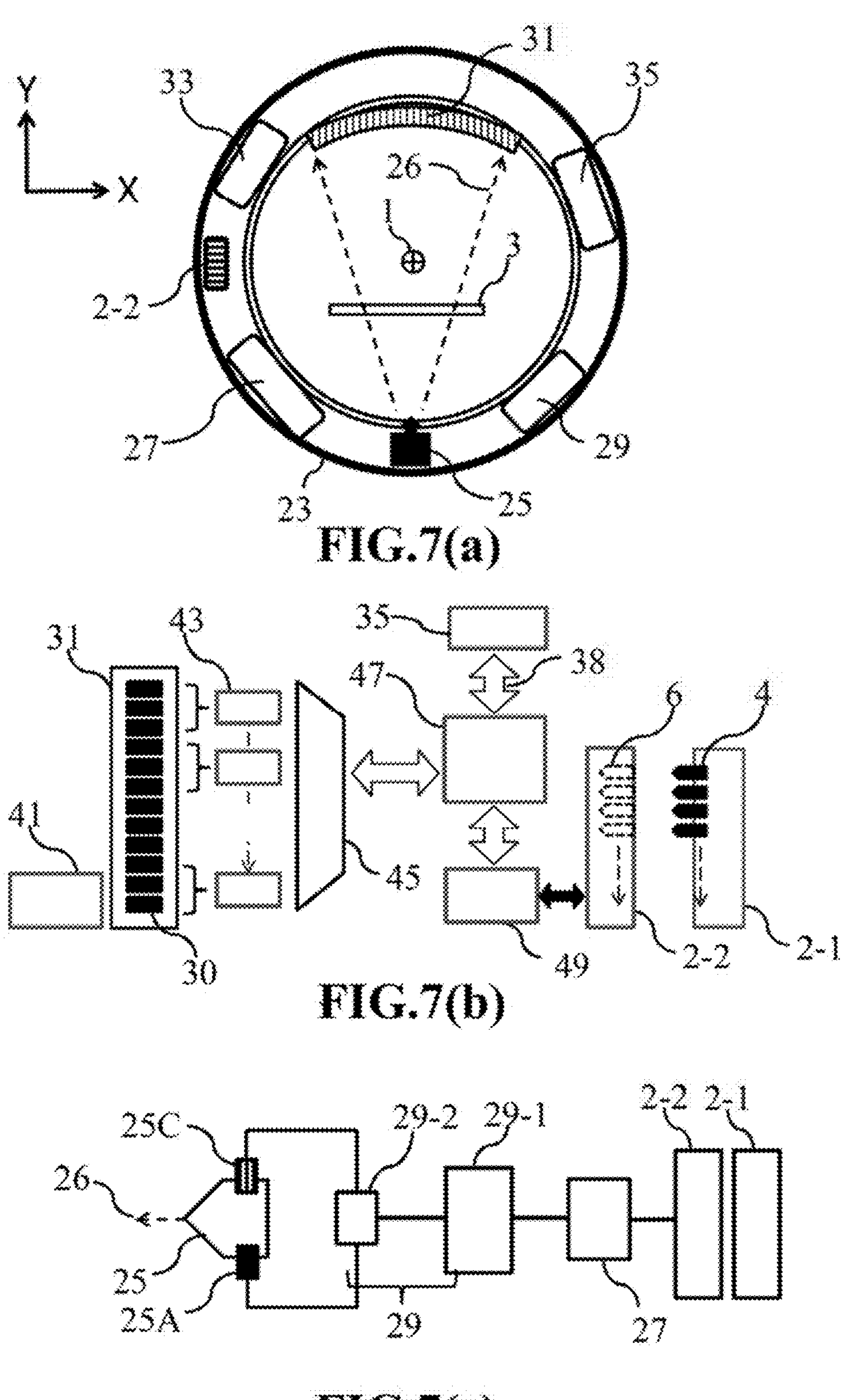
FIG. 7(*a*) is a plan view showing an internal structure of a rotating part in a CT, according to some example embodiments.

With reference to FIGS. 7(*a*)-7(*c*), the CT structure of a CT, particularly the structure of the rotating part 23 of the CT, will be described according to some example embodiments. It will be understood that any of the CTs according to any of the example embodiments, including any of CT 61, CT 61-2, CT 63, CT 63-2, CT 65, CT 67-1, CT 67-2, CT 69-1, and/or CT 69-2, may have a rotating part 23 having the same structure as shown in FIGS. 7(*a*)-7(*c*) and/or may include at least some of the elements of the rotating part 23 as shown in FIGS. 7(*a*)-7(*c*).

FIG. 7(*a*) is a plan view of a main part of the internal structure of the rotating part 23 inside the gantry 5 viewed from the Z-axis direction. A light source such as an X-ray generator 25, a light source drive circuit 29, a detector array 31, a detector peripheral circuit 33, an image memory 35, a rechargeable battery 27, and a rotating part interface 2-2 are provided in the rotating part 23. The X-ray beam 26 emitted from the X-ray generator 25 passes through the subject (not shown in FIG. 7(*a*)) placed on the bed 3 and reaches the detector array 31. A weight balancer (not shown in FIG. 7(*a*)) for adjusting the weight balance during rotation of the rotating part 23 may be provided (e.g., included in the rotating part 23). In some example embodiments, an X-ray generator using a carbon nanomaterial such as carbon nanotube (CNT) as a field electron emission source is used for the X-ray generator 25. Using the carbon nanomaterial as the cold cathode without preheating, it becomes possible to reduce the size and power consumption of the X-ray generator as compared with the conventional X-ray tube. In addition, the light source drive circuit 29 and a cooling fan can be downsized, or the cooling fan itself may be eliminated. In some example embodiments, the detector array 31 is built in the rotating part 23. As will be described later, the detector array 31 may be not located inside the rotating part 23 but may be located over the entire inner circumference of the gantry 5 surrounding the rotating part 23 (see FIG. 8(*c*), for example).

FIG. 7(*b*) is a circuit block diagram showing the inside of the rotating part 23 in FIG. 7(*a*), particularly the detector array 31 and its peripheral circuit 33. As shown in FIG. 7(*b*), the peripheral circuit 33 in FIG. 7(*a*) includes a detector driving and control circuit 41, a signal amplifying and analog-to-digital (AD) conversion circuit 43, a signal scanning and control circuit 45, and digital signal processing circuit 47, and a parallel to serial conversion circuit 49. As shown in FIG. 7(*b*), a plurality of sensor units 30 (also referred to interchangeably as sensors) are regularly arranged in an arc shape and in the Z-axis direction in order to increase the number (e.g., quantity) of slices in the detector array 31. The sensor unit 30 may use a small photo-electron multiplier type sensor (such as "micro PMT element" manufactured by Hamamatsu Photonics Co., Ltd.), an amplification type sensor utilizing an avalanche effect (APD), and a photon counting type sensor, for example. A CMOS or a CCD type sensor having on-chip analog-to-digital (AD) conversion circuit can be used, which will realize high-speed signal readout with lower noise can be realized. These sensor units have higher sensitivity and lower noise, and therefore a conventional large area detector with a larger number of slices using a TFT being laminated on a glass substrate for example, may not be necessarily required. With this configuration, the amount of total X-ray irradiation (exposure) can be reduced, or higher scanning speed in the Z-axis direction by shorter pulse width irradiation may be easily realized. Further, as will be described later, it will not be necessary to increase the applied voltage and an electrical current required for the X-ray generating part because it is not necessary to expand the X-ray irradiation area. In addition to the weight reduction by thinning the rotating part 23 in the Z-axis direction, the stability and durability of the carbon nanomaterial used as a field electron emission source can be improved.

The detector signal output from the detector array 31 is converted into digital data (16 bits for example) by the signal amplifying and the analog-to-digital (AD) conversion circuit 43 and sent to the digital signal processing circuit 47 via the signal scanning and control circuit 45, being followed by necessary image processing. The rotating part 23 has an internal image memory device 35 in order to directly record the image data sent from the digital signal processing circuit 47. Direct parallel and high-speed recording can be performed into the image memory device 35 via the bus-line 38 without parallel to serial conversion process. A magnetic recording medium can be used as the image memory device 35. In some example embodiments, a semiconductor non-volatile memory such as a NAND type flash memory is suitable from the viewpoint of recording speed and reliability. In some example embodiments, in the case when reading image data from the image memory device 35 after the completion of imaging step with the rotation of the rotating part 23 or the movement of the gantry 5 being stopped, it may not be necessary to read the image data in real time because the serial data can be output to the host interface 2-1 via the parallel to serial conversion circuit 49. The number (e.g., quantity) of terminals in the host interface 2-1 may be reduced by this serialization. In the electrical connection means including the host interface 2-1 and the rotating part interface 2-2, there are a plurality of connectors 6 inside the rotating part interface 2-2 of the rotating part 23, and each connector has a concave and female shape. There are more than one of connectors 4 at the side of the host interface 2-1 on the upper part of the gantry table 7, and each connector 4 has the shape of convex. Electrical connection is performed by inserting the connector 4 into the connector 6. Without using the mechanical electrical contacts like slip rings, the image data recorded and accumulated inside the rotating part 23 can be read out from the rotating part interface 2-2 to the host interface 2-1 when the rotating part 23 is stationary. Therefore, the above-mentioned adverse effects when using the slip rings may be eliminated, and high-speed rotation of the rotating part 23, such as 5 rotations or more per second for example, can be achieved. With this configuration, the amount of X-ray exposure can be reduced because the gantry 5 can be moved at high speed in the body axis (Z-axis) direction using a high-sensitivity, low-noise sensor and increasing the rotation speed of the rotating part 23 by reducing the weight of the rotating part 23 without increasing the number (e.g., quantity) of slices.

FIG. 7(*c*) shows a block diagram showing the X-ray generator 25 and the light source drive circuit 29 inside the rotation part 23. The X-ray generator 25 comprises an electron beam generation cold cathode 25C using carbon nanomaterials and an anode target 25A. The light source drive circuit 29 includes a voltage booster circuit 29-1 and a high voltage control circuit 29-2. In some example embodiments, the high voltage control circuit 29-2 is a transformer-less high-voltage power supply unit of small size, light weight, and low power consumption using a switching power supply and a power semiconductor chip. As for the rechargeable battery 27, a lithium-ion battery can be used, for example. The DC voltage of the lithium-ion battery 27 can be boosted by the high voltage control circuit 29-2, and a timing controlled high-voltage pulse can be applied to the X-ray generator 25. The remaining charges in the lithium-ion battery 27 may be monitored and the lithium-ion battery 27 can be charged by the charger circuit (not shown in FIG. 7(*c*)) via the rotating part interface 2-2 and the host interface 2-1 during the rotating part 23 being stationary.

Figures 8A, 8B, 8C, 8D:
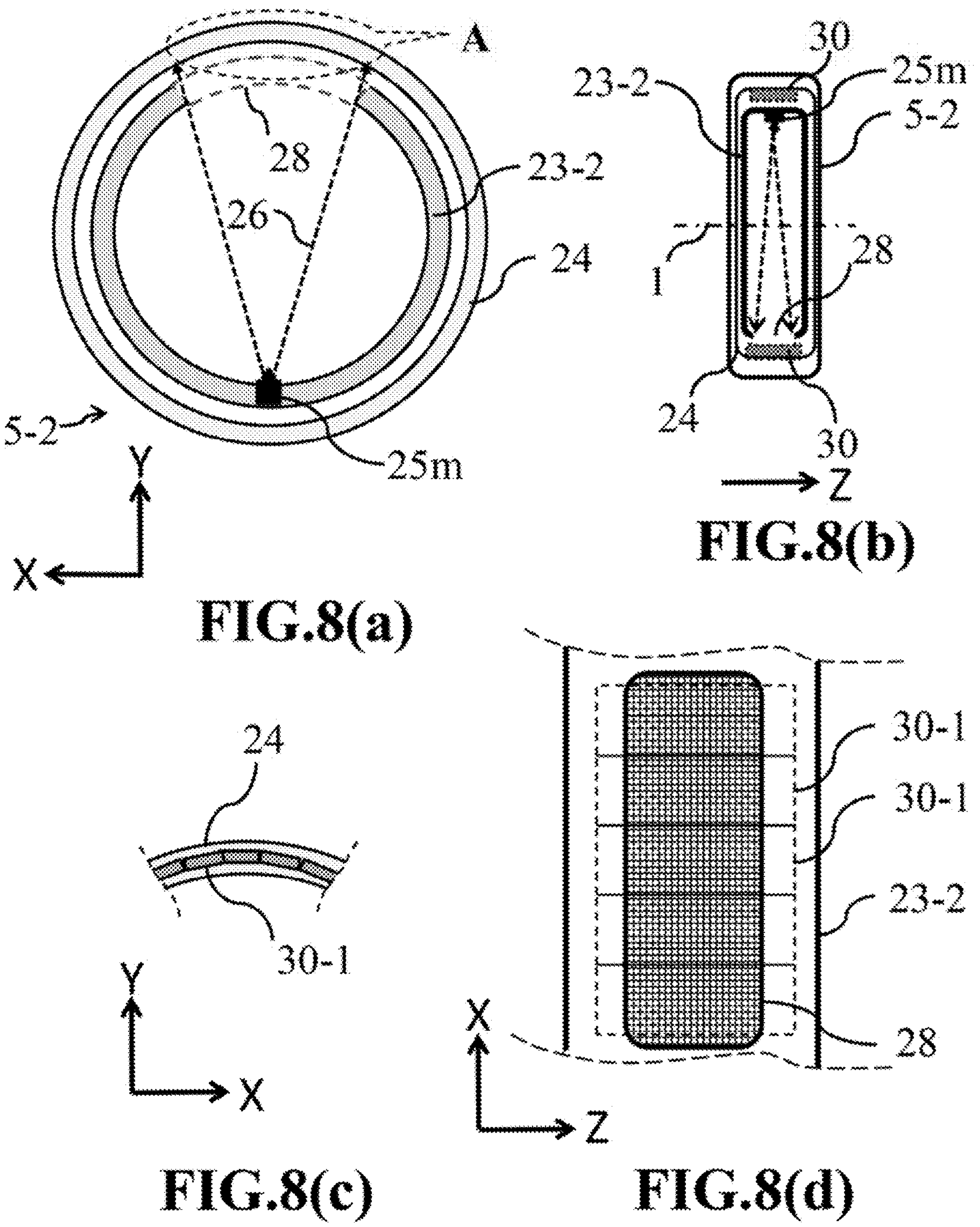
FIG. 8(*a*) is the X-Y plane view seen from a Z-axis direction showing another gantry structure suitable for a CT, according to some example embodiments.

FIG. 8(*a*) shows a plan view illustrating the structure of the CT according to some example embodiments, particularly inside the gantry part, as viewed from the Z-axis direction. It will be understood that any of the CTs according to any of the example embodiments, including any of CT 61, CT 61-2, CT 63, CT 63-2, CT 65, CT 67-1, CT 67-2, CT 69-1, and/or CT 69-2, may include the same structure as shown in FIG. 8(*a*) and/or may include at least some of the elements shown in FIG. 8(*a*). The fixed part 24 and the rotating part 23-2 are incorporated inside the gantry 5-2. The diameter of the rotating part 23-2 containing the X-ray generator 25*m* is smaller than the diameter of the inner peripheral portion of the fixed part 24. The X-rays emitted from X-ray generator 25*m* can reach the detector array without being blocked by the fixed part 24. This setup may be like so-called Stationary Rotate type CT. However, in the case of the conventional structure using a slip ring and electrode brush, their contact surface may heat up causing seizure, and the detector array may make an erroneous photoelectric conversion of incident X-rays due to a light emission phenomenon caused by an electric spark when a high voltage or large current flow is applied from the brush electrode to the slip ring sliding with a high speed. In addition, conventionally, this configuration may cause non-uniform X-ray irradiation of the detector array because the rotating part 23-2 is located opposed to the X-ray generator 25*m* in between the central axis of the rotation center and on the optical path of the X-ray beams 26 emitted from the X-ray generator 25*m*. A structure that solves this problem will be described below with reference to FIGS. 8(*a*)-8(*d*). It will be understood that any of the CTs according to any of the example embodiments, including any of CT 61, CT 61-2, CT 63, CT 63-2, CT 65, CT 67-1, CT 67-2, CT 69-1, and/or CT 69-2, may include the same structure as shown in FIGS. 8(*a*)-8(*d*) and/or may include at least some of the elements shown in FIGS. 8(*a*)-8(*d*).

As described above, the fixed part 24 is combined to surround the outer circumference of the rotating part 23-2. A detector array (not shown in FIG. 8(*a*)) may be arranged on the entire inner circumference of the fixed part 24. The rotating part 23-2 has an X-ray generator 25*m*, a light source drive circuit and a rechargeable battery (not shown in FIG. 8(*a*)), for example. An opening 28 marked by a broken line A is formed at the rotating part 23-2 so that the X-ray beams 26 emitted from the X-ray generator 25*m* can transmit or pass therethrough. With this configuration, intensity of X-ray beam 26 and its traveling direction may not be affected. The opening 28 does not necessarily have to be an empty space where all the members are removed (air only), but a subject protector made of resin having a high X-ray transmittance, for example, may exist.

FIG. 8(*b*) is a cross-sectional view of the structure inside the gantry (e.g., gantry 5-2 of FIG. 8(*a*)) when the opening 28 is viewed from the X-axis or Y-axis direction. The sensor units 30 are arranged along the inner circumference of the fixed part 24, and the X-ray beam passing through the opening 28 reaches the sensor units 30. A fiber optic plate which selectively shields or collimates X-rays, and an X-ray scintillator, for example, may be stacked on the sensor units 30.

FIG. 8(*c*) is an enlarged plan view seen from the Z-axis direction showing the structure of the portion indicated by the broken line A in FIG. 8(*a*). The CMOS-type sensor units 30-1, for example, are closely arranged along the annular portion of the fixed part 24 so that the longitudinal direction of the sensor units 30-1 are parallel to the Z-axis.

FIG. 8(*d*) shows the same portion with reference to a plan view of the opening 28 being observed from the side of X-ray generator 25*m*. The pixel arrays of the sensor units 30-1 attached to the fixed part 24 are directly exposed to the X-ray generator 25*m* through the opening 28 formed in the rotating part 23-2 without shielding the X-ray irradiation. Accordingly, it will be understood that the rotating part 23 may have an opening 28 that is configured to admit light (e.g., incident light, such as X-ray light) that is emitted by a light source (e.g., X-ray generator 25*m*) that is mounted on the rotating part 23 to pass through the opening 28 to irradiate at least a portion of the detector array 31.

With reference to FIGS. 9(*a*)-9(*c*), arrangement and combination of sensor units 30-1 which may be suitable for the CT used in the medical vehicle will be described below according to some example embodiments. It will be understood that any of the CTs according to any of the example embodiments, including any of CT 61, CT 61-2, CT 63, CT 63-2, CT 65, CT 67-1, CT 67-2, CT 69-1, and/or CT 69-2, may include one or more sensor units that may include the same structure as shown in FIGS. 9(*a*)-9(*c*) and/or may include at least some of the elements shown in FIGS. 9(*a*)-9(*c*).

In FIG. 9(*a*), a plurality of sensor units 30-1 are closely arranged along the inner circumference of the fixed part 24 as to surround the rotation center axis 1. As shown in FIG. 9(*a*), peripheral circuits such as the vertical scanning circuit (30-12), and the horizontal scanning and the signal readout circuits (30-13) are placed along the two sides opposite to each other around the rectangular light receiving region where many pixels 30-11 are arranged vertically and horizontally. Pixels 30-11 are arranged on the remaining two opposite sides even at the end of the light receiving region. Adjacent sensor units 30-1 of the plurality of sensor units 30-1 are contacted with and between adjacent boundary lines 30-14 that are each between separate adjacent sensor units 30-1, and in some example embodiments, the arrangement pitch of the pixels 30-11 in between adjacent boundary lines 30-14 is equal to the arrangement pitch of the pixels 30-11 being not contacted with one or more boundary lines 30-14 in the same direction. Further, as shown in FIG. 9(*a*), the plurality of sensor units 30-1 are placed along the two opposite sides along which the peripheral circuits are formed in order not to change the arrangement pitch of each pixel 30-11 in the direction of the rotation of the rotating part (e.g., rotating part 23). In some example embodiments, the sensor unit 30-1 has a larger chip size. So-called medium format size (44 mm×33 mm), full format size (36 mm×24 mm) and APS format size (23 mm×15 mm) sensor units which are widely used in digital cameras, for example, can be also used based on or optimizing their structure and manufacturing method of CMOS type sensor, and their design can be modified in accordance with the required specifications of the CT used in the present inventive concepts.

FIG. 9(*b*) shows a configuration where a plurality of sensor units 30-2 are closely arranged along the inner circumference of the fixed part 24 in FIGS. 8(*a*)-8(*c*) as to surround the rotation center axis 1 and further arranged in the direction of the rotation center axis 1 to increase the total number of pixels in the direction of body axis (Z-axis). With such a configuration, the slice width can be enlarged two-fold. In some example embodiments, the boundary line 30-24 between the left and right sensor units 30-2 is considered, because the arrangement pitch of the pixels 30-21 in between the boundary line 30-24 should be equal to the arrangement pitch of the other pixels 30-21 not facing the boundary line 30-24 in the same direction. As shown in FIG. 9(*b*), the vertical scanning circuit and the horizontal scanning and the signal readout circuits (30-22 and 30-23) are placed along the one side of the sensor units 30-2 in order not to change the arrangement pitch of each pixel 30-21 along the other three sides of the sensor units 30-2.

FIG. 9(*c*) is a detailed cross-sectional view of the sensor unit 30-2 as shown in FIG. 9(*b*). The sensor unit 30-2 is a backside illuminated CMOS solid-state image sensor having a scintillator layer 46 laminated on the backside. The silicon substrate used in this CMOS solid-state image sensor may be about 5-to-10-micron meter (μm) in thickness because the incident X-ray is converted into a visible light in the scintillator layer and the visible light is read out as an electric signal by each pixel 30-21. A wiring layer 30-27, horizontal and vertical scanning circuits, signal readout circuits (30-22, 30-23), and connection terminals 30-26 are provided on the front side of the sensor unit 30-2. On the back side, a shield member 30-25, which can reduce the X-ray intensity of incident X-rays and protect the integrated circuit from X-ray damage, is laminated on the horizontal scanning, vertical scanning and the signal readout circuits (30-22 and 30-23). With the CMOS type solid-state image sensor using a silicon substrate, the thickness of the substrate can be reduced to 10-micron meter (μm) or less, so that the sensor unit itself can be curved with respect to the direction of the incident light. As a result, the sensitivity dependence on the incident angle of the X-ray may be reduced. With this structure, low noise, high sensitivity, and high-speed imaging in the CT are realized. As a result, radiation exposure problem due to X-rays may also be reduced, while it used to be difficult to use a conventional CMOS type sensor as for an X-ray detector.

Examples of CT used in a medical vehicle will be described with reference to FIGS. 10(*a*)-10(*e*) according to some example embodiments. It will be understood that any of the CTs according to any of the example embodiments, including any of CT 61, CT 61-2, CT 63, CT 63-2, CT 65, CT 67-1, CT 67-2, CT 69-1, and/or CT 69-2, may include the same structure as the CT 63 shown in FIGS. 10(*a*)-10(*e*) and/or may include at least some of the elements of CT 63 as shown in FIGS. 10(*a*)-10(*e*).

Figures 10A, 10B, 10C, 10D, 10E:
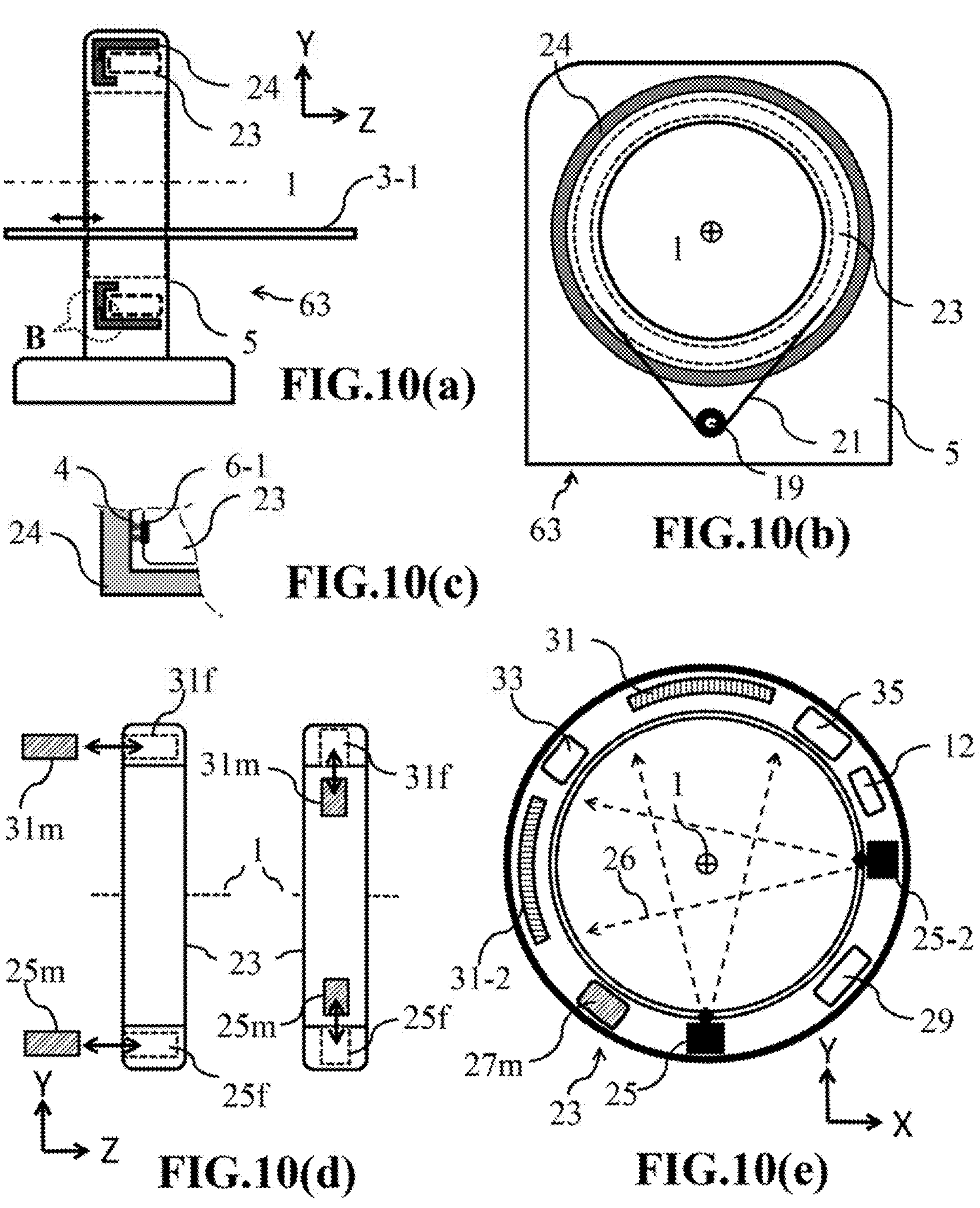
FIG. 10(*a*) is a side view of a CT used in a medical vehicle as viewed from an X-axis direction, according to some example embodiments.

FIG. 10(*a*) shows a side view of the CT 63 as viewed from the X-axis direction. The CT 63 takes an image during a bed 3-1 is moving in the body axis direction while the gantry 5 is stationary. The CT 63 comprises a bed 3-1, a bed supporting member (not shown in FIG. 10(*a*)) for moving or supporting the bed 3-1 and the gantry 5 having annular cavity. The gantry 5 has the rotatable rotating part 23 inside, and the rotation center axis 1 is parallel to the Z-axis, or the body axis direction. A fixed part 24 is placed around the rotating part 23 using a ball bearing (not shown in FIG. 10(*a*)), for example. An operation or control unit and a display monitor unit (not shown in FIG. 10(*a*)) are provided, and a reconstructed tomographic image generated by an image processing circuit and software may be displayed on the display. A portion B surrounded by a broken line with respect to the rotating part 23 and the fixed part 24 will be discussed in detail below.

FIG. 10(*b*) is a plan view of the CT 63 seen from the Z-axis direction. Inside the annular portion of the gantry 5, a rotating part 23 that rotates around the rotation center axis 1 is installed using ball bearings (not shown in FIG. 10(*b*)). A timing belt 21 for rotating the rotating part 23 and a rotating part drive motor 19 are installed. As will be described below, a direct drive (DD) motor configuration may be also used such that the rotating part 23 acts as a rotor and the inner circumference of the gantry 5 surrounding the rotating part 23 acts as a stator.

FIG. 10(*c*) shows an enlarged view of the portion B in FIG. 10(*a*), and the rotating part interface 6-1 made of a metal electrode is formed on the side surface of the rotating part 23. The rotating part interface 6-1 is located at a position facing the host interface of the convex type of connection terminals 4. The rotating part interface 6-1 can be electrically connected to the connection terminals 4 of the host interface 2-1 based on the rotating part interface 6-1 and the connection terminals 4 of the host interface 2-1 contacting each other when the rotating part 23 is stationary. In some example embodiments, a position sensor (not shown in FIG. 10(*c*)) using a Hall effect position sensor, for example may be used so that the convex connection terminal 4 and the rotating part interface 6-1 are stopped at a position facing each other, such that the rotating part interface 6-1 and the convex connection terminal 4 of the host interface 2-1 are face to face with each other as described herein. In some example embodiments, if the rotating part interface 6-1 is formed in a ring shape over the entire circumference of the annular side surface of the rotating part 23, the rotating part interface 6-1 may be electrically connected regardless of the stationary position of the rotating part 23. Low-voltage and low-current signals such as control signals and image data signals can be transmitted to and received from the fixed part 24 via the ring shape rotating part interface even when the rotating part 23 is rotating. In some example embodiments, as described above, the electrical power to the light source like the X-ray generator may be supplied by the rechargeable battery installed inside the rotating part without using a mechanical contact like the ring shape rotating part interface. The arrangement of the connection terminal 4 and the rotating part interface 6-1 is not limited to the case of contact in the Z-axis direction as shown in the drawing and may be in the direction toward the central axis 1 (Y-axis direction).

FIG. 10(*d*) is a cross-sectional view of the CT 63 showing the rotating part 23 seen from the X axis direction, according to some example embodiments. The X-ray generator 25*m*, which is a component incorporated in the rotating part 23, should be replaced corresponding to the frequency of use due to the deterioration of the target member, and consumption of the electron beam generating cathode materials. Similarly, the detector array 31*m* may also need to be replaced due to the radiation damage to their semiconductor components or the humidity dependency of the laminated X-ray scintillator material. Therefore, in some example embodiments, the X-ray generator 25*m* and the detector array 31*m* employs cartridge form, which is detachable from the rotation part 23 in Z axis direction. As shown at the left-hand side of FIG. 10(*d*), the rotating part 23 is provided with cartridge receiving spaces 25*f* and 31*f* (both indicated by broken lines) into which the cartridge types X-ray generator 25*m* and the detector array 31*m* can be inserted. This cartridge form is not limited to the X-ray generator and the detector array, but a rechargeable battery or an image memory may have such a cartridge form due to the increase in power consumption or in recording memory capacity. In some example embodiments, the cartridge receiving spaces having individual openings on the inner peripheral surface of the gantry parallel to the central axis are provided (right side of FIG. 10(*d*)). The cartridge types of light source, detector, image memory, or rechargeable battery may be inserted or removed into or from the openings directed from the central axis to the normal direction of the outer periphery of the rotating part. With these structures, it is not necessary to remove the gantry cover in order to repair defective parts or change with a new part individually but only the defective part of the cartridge structure can be replaced by removing or opening the individual cover for the corresponding opening. As a result, CT can be easily and quickly returned to normal operation, and the downtime of the CT can be reduced or minimized. As described above, introducing the cartridge structure for major parts, it becomes easy to deal with the event of breakdown of a CT even when the medical vehicle including the CT is at a remote place. In addition, regular maintenance load associated with the CT and/or medical vehicle including same may be remarkably reduced.

FIG. 10(*e*) is a plan view of the CT rotating part 23 according to some example embodiments as viewed from the Z-axis direction. In addition to a cartridge type rechargeable battery 27*m*, a light source drive circuit 29, a detector peripheral circuit 33, an image memory 35, and a wireless rotating part interface 12, in some example embodiments, further the first X-ray generator 25, the second X-ray generator 25-2, the first detector array 31, and the second detector array 31-2 are arranged where each X-ray detector is facing each detector array via the central axis 1, respectively. The detector array 31 and the detector array 31-2 may be arranged at positions shifted in the Z-axis direction. In some example embodiments the X-ray generator 25 and the X-ray generator 25-2 may irradiate X-rays at the same time or may irradiate with a time lag. Further, different high voltages for different wavelengths may be applied to the X-ray generators 25 and 25-2 to perform multi-spectral analysis. With these configurations, it becomes easy to perform various imaging under different examination conditions, and more accurate diagnosis can be realized despite the miniaturization and weight reduction of the CT.

In view of at least FIGS. 10(*a*)-10(*e*), a CT gantry 5 may include a light source that is a detachable cartridge and thus has a detachable cartridge form (e.g., X-ray generator 25*m*), a detector that is a detachable cartridge and thus has a detachable cartridge form (e.g., detector array 31*m*), and/or a rechargeable battery that is a detachable cartridge and thus has a detachable cartridge form (e.g., rechargeable battery 27*m*).

Figures 11A, 11B, 11C, 11D:
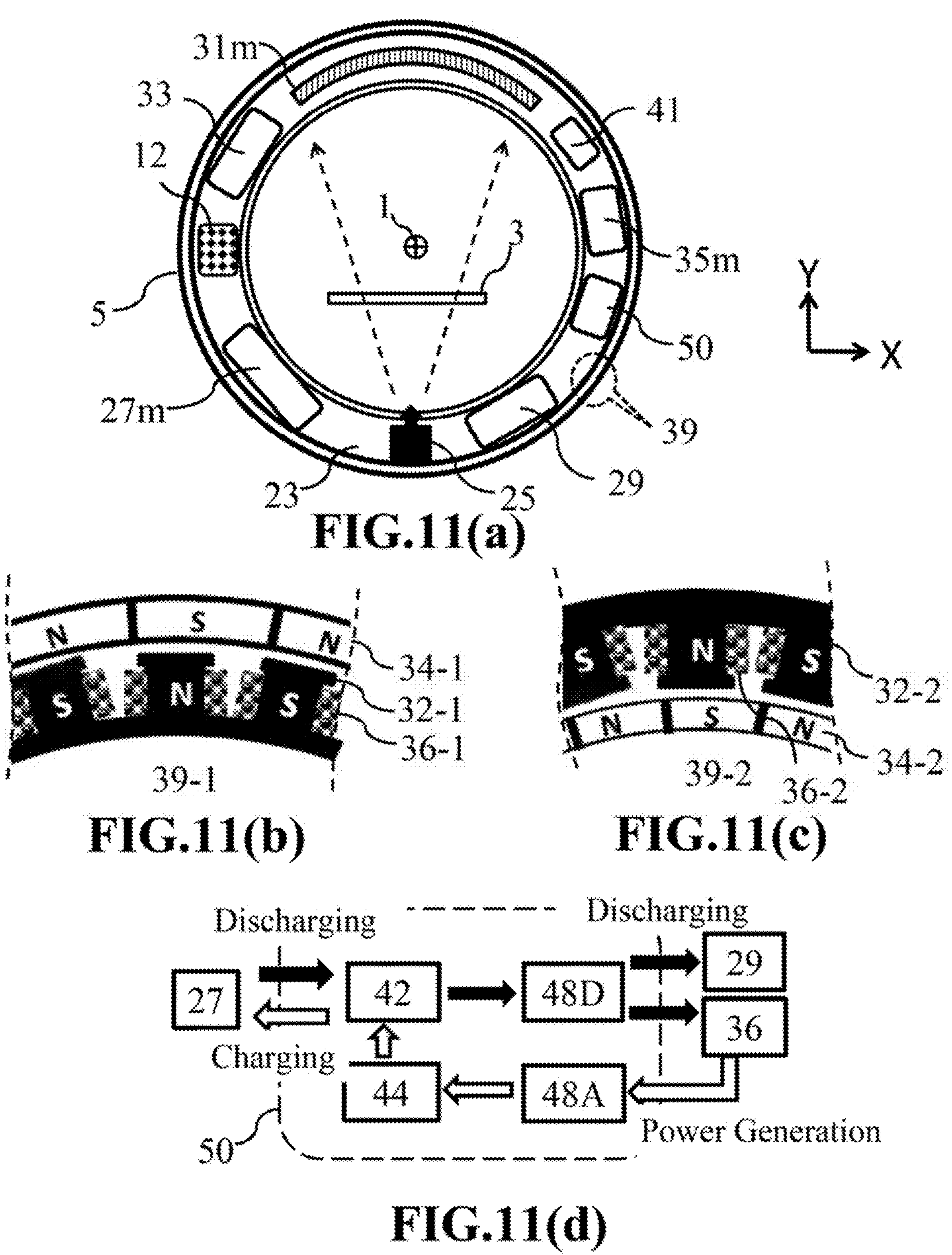
FIG. 11(*a*) is a plan view illustrating the structure of a rotating part inside a gantry of a CT, according to some example embodiments.

With reference to FIGS. 11(*a*)-11(*d*), the rotating part of the CT suitable for the medical vehicle, particularly inside the gantry is described according to some example embodiments. It will be understood that any of the CTs according to any of the example embodiments, including any of CT 61, CT 61-2, CT 63, CT 63-2, CT 65, CT 67-1, CT 67-2, CT 69-1, and/or CT 69-2, may include the same structure as shown in FIGS. 11(*a*)-11(*d*) and/or may include at least some of the elements as shown in FIGS. 11(*a*)-11(*d*), for example at least some or all of the structure of the rotating part 23 as shown in FIGS. 11(*a*)-11(*d*).

FIG. 11(*a*) shows a plan view of the rotating part 23 inside the gantry 5 as seen from the Z-axis direction. As shown in FIG. 11(*a*), the rotation part 23 has the X-ray generator 25, the rechargeable battery 27*m* with a cartridge form, the light source drive circuit 29, the detector array 31 with a cartridge form, the detector peripheral circuits 33 including the signal amplification circuit, AD conversion circuit and the signal scanning or control circuits, the semiconductor image memory 35*m* with a cartridge form, the detector driving and control circuit 41, a contactless interface 12, a digital signal processing circuit, and a parallel to serial conversion circuit (not shown in FIG. 11(*a*)) are incorporated inside the rotation part 23. As will be described below, in some example embodiments an energy recovery brake circuit 50 is placed (e.g., is located) in the fixed part or the rotating part 23 inside the gantry 5. Electromagnetic induction coils and permanent magnets to face each other are arranged around either the rotating part 23 or the fixed part. In the present inventive concepts, the term "energy recovery brake circuit" is used for convenience, however, as described in detail below, which is not limited to the case where the kinetic energy is recovered as electrical energy when the rotating part 23 decelerates but the circuit can be used when the rotating part is forcibly rotated for converting kinetic energy into electrical energy to generate continuous electric power which will charge the rechargeable battery inside the rotating part, for example.

FIGS. 11(*b*) and 11(*c*) show the enlarged structure of the broken line portion 39 in FIG. 11(*a*). In the structure (39-1), for example, the N pole and the S pole of the permanent magnet (34-1) are alternately arranged along the ring-shaped side of the fixed part (e.g., along an entire inner circumference of the fixed part). On the side of the rotating part 23, the induction coils (36-1) are wound around the iron cores (32-1). The energy recovery brake circuit 50 may be provided inside the rotating part 23.

Referring to FIGS. 11(*a*)-11(*b*), in some example embodiments a CT may include a rotating part 23 inside the CT gantry 5 and a fixed part surrounding the rotating part 23 inside the CT gantry 5, where the rotating part 23 may include a light source (e.g., X-ray generator 25*m*), a rechargeable battery (e.g., rechargeable battery 27*m*) an energy recovery brake circuit (e.g., energy recovery brake circuit 50), and induction coils (e.g., 36-1) that are arranged around an annular part of the rotating part 23, and the fixed part may include permanent magnets (e.g., 34-1) of N-poles and S-poles facing the induction coils (e.g., 36-1) and alternately arranged along an entire inner circumference of a fixed part inside the CT gantry 5.

In some example embodiments, in the structure (39-2) of FIG. 11(*c*), the N pole and the S pole of the permanent magnet (34-2) are alternately arranged along the ring-shaped side of the rotating part 23, and the induction coils (36-2) are wound around the iron cores (32-2) on the side of the fixed part. The energy recovery brake circuit 50 and a rechargeable battery (e.g., 27, 27*m*, etc.) may be provided inside the fixed part.

As will be described later, the structure shown in FIG. 11(*b*) may be preferable if electric energy is stored in the rechargeable battery (e.g., 27, 27*m*, etc.) or the electric double layer capacitor inside the rotating part 23 because the rotational kinetic energy can be recovered as an electric energy to the rechargeable battery or the electric double layer capacitor in the rotating part until the rotation is stopped after providing the forcible rotational motion during imaging. In the structure of FIG. 11(*b*), when the rotating part 23 is forcibly rotated by an external motor via a timing belt, an electromotive force is generated in the induction coil (36-1) to supply electric power to the light source in the rotating part reducing the battery load of the rechargeable battery 27.

In some example embodiments, the structure shown in FIG. 11(*c*) is also a structure of a DD motor, which will not require an external motor and a timing belt like a case of the CT 61-2 in FIG. 5(*c*). In this case, the energy recovery brake circuit 50 and a rechargeable battery 27*m* are placed in the fixed part because the induction coils (36-2) are wound around the iron cores (32-2) on the side of the fixed part.

As described above, conventionally, regenerative resistors are used to dissipate the electrical energy generated in the rotating part drive motor 19 (see, e.g., FIG. 5(*c*)) due to the kinetic energy of the rotating part 23 after the CT imaging. As a result, the generated electrical energy radiates and diffuse as Joule heat to the outside. In such a case, the temperature of the CT may rise, and the load on the cooling device for both the CT and air conditioning system may increase. In some example embodiments, the timing belt 21 in FIG. 5(*c*) will be mechanically released or unlocked with the shaft of the drive motor 19 when the CT imaging operation is completed, for example. With this configuration, the kinetic energy of the rotating part 23 can successfully recover as an electric energy to charge the rechargeable battery or the electric double layer capacitor without increasing temperature and wasting energy from the point of view of global warming.

In some example embodiments, a neodymium magnet may be used for the permanent magnet (e.g., 34-1 and/or 34-2) for example. The rotational movement of the rotating part inside the gantry may be unnecessary after the imaging operation is completed. However, it may be possible to convert the moment of inertia of the rotating part into an electric energy without stopping the rotary motion mechanically. As a result, energy saving effect can be obtained. The energy recovery brake circuit 50 has such a role in some example embodiments. Regarding the CT, rotation (imaging mode) and stop (standby mode) motions are frequently repeated, so the above-mentioned rotation energy recovery effect of the rotating part is remarkable, particularly, in the case of high-speed scanning with increasing the number of rotations of the rotating part.

The energy recovery brake circuit 50 is described below with reference to FIG. 11(*d*). In the CT according to some example embodiments, the imaging operation starts after the rotation of the rotating part 23 starts. The rotation of the rotating part 23 may decelerate and the rotational motion may stop after completing the imaging sequence. As described above, rotation start and stop motions are repeated within imaging operations in a brief period. Effective reuse of the rotational kinetic energy of the rotating part 23 may reduce the power consumption of the rechargeable battery 27 and save energy. The FIG. 11(*d*) is a circuit configuration for explaining the energy recovery brake circuit 50 provided inside the rotating part 23. One end of the bidirectional DC-DC converter 42 is connected to the rechargeable battery 27. A DC-AC converter 48D connected to the other end (e.g., opposite end) of the bidirectional DC-DC converter 42. The other end of the DC-AC converter 48D is connected to the light source drive circuit 29 and the induction coil 36. The induction coil 36 is connected to a capacitor, preferably an electric double layer capacitor 44 via an AC-DC converter 48A. Further, the electric double layer capacitor 44 is connected to the bidirectional DC-DC converter 42. The rotary kinetic energy of the rotating part 23 can be converted into counter electromotive force generated in the induction coil 36, which can charge the electric double layer capacitor 44. Also, the rechargeable battery 27 can be charged after being converted to a particular (or, alternatively, predetermined) voltage via the bidirectional DC-DC converter 42. As described above, during the CT imaging, an electromotive force is generated in the induction coil (36-1) when the rotating part 23 is forcibly rotated by an external motor via a timing belt, which can be used to drive the light source drive circuit 29 or the like in the rotating part. Further, this structure is useful even when the CT imaging is stopped other than when the CT imaging is performed because the rechargeable battery built in the rotating part 23 can be charged by forcibly rotating the rotating part 23 via the timing belt by an external motor. In this case, the rotation speed $n_2$ of the rotating part during non-CT imaging process can be set arbitrarily since the CT imaging is not involved. In some example embodiments, when the rotation speed of the rotating part at the time of CT imaging is $n_1$, the rotation speed $n_2$ is increased more than the rotation speed $n_1$ ($n_2>n_1$) to charge the rechargeable battery at a higher charging speed. As shown in FIG. 11(*d*), an electric power is generated by the induction coil 36, the capacitor 44 is charged via the AC-DC converter 48A, and the rechargeable battery 27 is further charged via the bidirectional DC-DC converter 42. This eliminates the need for power supply via the slip ring, which will improve the reliability of the CT, reduce the maintenance load, and will be particularly suitable as a structure and driving method of the CT used in a medical vehicle.

The driving method when the energy recovery brake is used in some example embodiments will be described. After the rotation of the rotating part 23 is started, then the bed or the gantry begins to move. Next, imaging by X-ray irradiation proceeds. The digital data obtained from the detector array 31 is recorded in the image memory in a real time manner. As described above, digital data can be recorded in the image memory as parallel data without converting the data from parallel to serial. In some example embodiments, the wireless communication interface, which is explained with reference to the FIGS. 6(*a*) and (*b*), can be used to record the digital data directly into a storage unit in the control unit 22-1, for example. After the imaging is completed, the rotational kinetic energy of the rotating part 23 causes a counter electromotive force in the induction coil(s) to be recovered as an electric energy, and the rotational movement is decelerated while charging the capacitor or the rechargeable battery. Finally, the gantry stops at a particular (or, alternatively, predetermined) position, the data recorded in the image memory is read from the rotating part interface through the host interface, and the image is reconstructed by the operation and control unit, and the shooting image is displayed on the display monitor. In parallel, the rechargeable battery is charged. Subsequently, a series of sequences is completed to enter the standby state.

In general, the energy recovery efficiency using a capacitor may be about 90% or more, which may be higher than that of the case using a rechargeable battery of around 60% efficiency. Particularly, with this configuration, it may be useful for the CT in which the rotating part 23 is decelerated (energy recovery) and is immediately rotated (discharged) repeatedly. With respect to the bidirectional DC-DC converter 42, a circuit system in which a step-down chopper circuit and a step-up chopper circuit are combined, or a PWM (Pulse Width Modulation) system using a DSP (Digital Signal Processor) and an AD converter may be used. In the above embodiments, a direct drive (DD) motor configuration is also available, where an AC voltage generated by the rechargeable battery 27 inside the rotating part 23 is applied to the electromagnetic induction coil 36-1 to rotate the rotating part 23 such that the rotating part 23 acts as a rotor and the inner circumference of the gantry 5 surrounding the rotating part 23 acts as a stator.

Figures 12A, 12B, 12C, 12D:
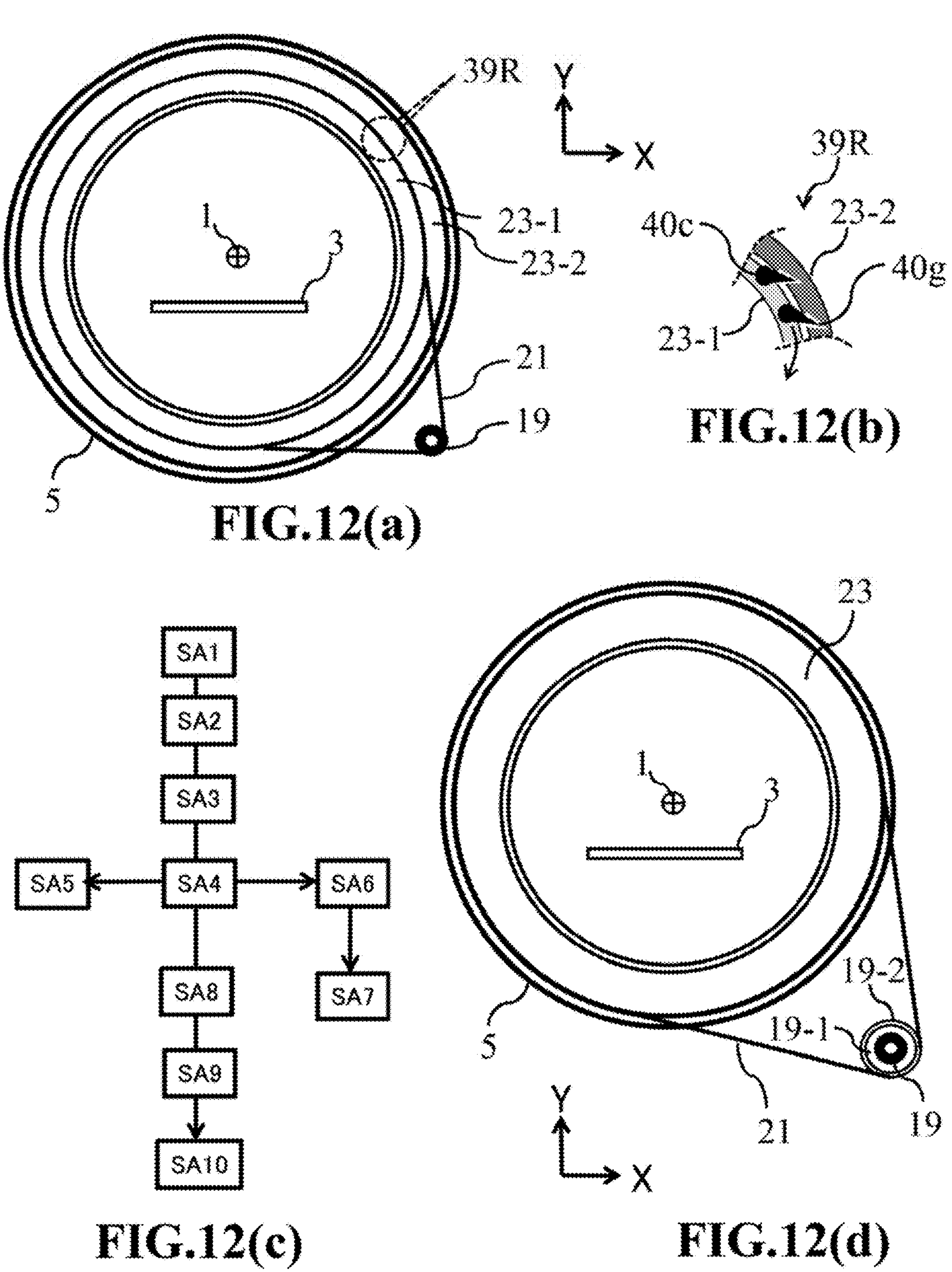
FIG. 12(*a*) is a plan view showing an internal structure of a gantry of a CT, according to some example embodiments.

Referring to FIGS. 12(*a*) to 12(*d*), the CT may further include a ratchet mechanism (also referred to herein interchangeably as a ratchet structure), where the ratchet mechanism and a timing belt 21 are configured to be mechanically interlocked with a shaft of a drive motor 19 in a first rotational direction of the timing belt 21, and the ratchet mechanism and the timing belt 21 are configured to be mechanically released from the shaft of the drive motor 19 in a decelerated timing belt rotational speed, or an opposite, second timing belt rotational direction. As shown in FIGS. 12(*a*) and 12(*b*), the ratchet mechanism may be included in the rotating part 23 (e.g., as moveable claws 40*c* and grooves 40*g* in separate ones of rotating parts 23-1 and 23-2). As shown in FIGS. 12(*b*) and 12(*d*), the ratchet mechanism may be included in the drive motor 19 (e.g., as moveable claws 40*c* and grooves 40*g* in separate ones of rotating parts 19-1 and 19-2). It will be understood that the rotating part 23 and the drive motor 19 may each include a separate, respective ratchet mechanism (e.g., rotating part 23 may include the ratchet mechanism as shown in FIGS. 12(*a*) and 12(*b*) while drive motor includes a separate ratchet mechanism as shown in FIGS. 12(*d*) with regard to 12(*b*)).

FIGS. 12(*a*) to 12(*c*) show a structure of the rotating part inside the gantry and the driving method using the same, which is suitable for the CT used in a medical vehicle according to some example embodiments. It will be understood that any of the CTs according to any of the example embodiments, including any of CT 61, CT 61-2, CT 63, CT 63-2, CT 65, CT 67-1, CT 67-2, CT 69-1, and/or CT 69-2, may include the same structure as shown in FIGS. 11(*a*)-11(*d*) and/or may include at least some of the elements as shown in FIGS. 12(*a*)-12(*c*), for example at least some or all of the structure of the rotating part 23 as shown in FIGS. 12(*a*)-12(*c*). As described above, conventionally, regenerative resistors are used to dissipate the electrical energy generated in the rotating part drive motor 19 by the kinetic energy of the rotating part 23 via the timing belt 21 after the CT imaging. The generated electrical energy is consumed by the regenerative resistors radiating and diffusing as Joule heat to the outside. In some example embodiments, the timing belt 21 may be mechanically released or unlocked with the shaft of the drive motor 19 when the CT imaging operation is ended. With this configuration, the kinetic energy of the rotating part 23 may not be converted into an electric energy by the rotating part drive motor 19 via the timing belt 21.

FIG. 12(*a*) is a plan view of the gantry 5 viewed from the Z-axis direction. In some example embodiments, the rotating part 23 is composed of two rotating parts (23-1 and 23-2) which has a ratchet structure, also referred to herein interchangeably as a ratchet mechanism, where one rotating part (23-1 in FIG. 12(*a*)) is equipped with a timing belt 21 and the other rotating part (23-2 in FIG. 12(*a*)) can be mechanically interlocked with the one rotating part 23-1 depending on the rotational direction of the one rotating part 23-1. As shown, the two rotating parts 23-1 and 23-2 may have a same rotational axis and a ratchet mechanism in-between the two rotating parts 23-1 and 23-2. As shown in FIG. 12(*b*), the ratchet mechanism may include movable claws 40*c* and grooves 40*g* in separate, respective ones of the two rotating parts 23-1 and 23-2.

FIG. 12(*b*) is a partially enlarged view for explaining the structure of the broken line portion 39R in FIG. 12(*a*). As shown in FIG. 12(*b*), movable claws 40*c* are attached around the one rotating part 23-1. The claws 40*c* may fall in grooves 40*g* formed around an inner circumference of the other rotating part 23-2 and transmit torque when the rotating part 23-1 rotates clockwise. In some example embodiments, the claws 40*c* slip over the grooves 40*g* on the inner circumference of the other rotating part 23-2 without transmitting the torque to idle when the one rotating part 23-1 decelerates, stops, or rotates counterclockwise. Accordingly, a first rotating part 23-1 may be interlocked with a second rotating part 23-2, such that the ratchet structure and the timing belt 21 are mechanically interlocked with the shaft of the drive motor 19, based on the first rotating part 23-1 rotating in a first rotational direction (e.g., clockwise) in relation to the second rotating part 23-2 and may be released from the second rotating part 23-2, such that the ratchet structure and the timing belt 21 are mechanically released from the shaft of the drive motor 19, based on the first rotating part 23-1 decelerating (e.g., rotating in a decelerated rotational speed), stopping, and/or rotating in an opposite, second rotational direction (e.g., counterclockwise) in relation to the second rotating part 23-2. Changing the structure or direction of claws 40*c* and grooves 40*g*, the torque of one rotating part 23-1 can be transmitted to the other rotating part 23-2 when the rotating part 23-1 rotates either clockwise or counterclockwise, accordingly. Besides the claw ratchet structure as shown above, other ratchet types such as a ball ratchet structure, for example, may be selected appropriately. The ratchet structure may be a kind of a clutch structure such as a meshing clutch, a friction clutch, a centrifugal clutch, and an electromagnetic clutch.

In some example embodiments, the drive motor 19 may include the ratchet structure as shown in FIGS. 12(*a*) and 12(*b*) with regard to the rotating part. FIG. 12(*d*) is a plan view of the gantry 5 of a CT viewed from the Z-axis direction, according to some example embodiments. As shown in FIG. 12(*d*), in some example embodiments, the drive motor 19 may include a ratchet structure, such that the drive motor 19 may have two rotating parts (19-1 and 19-2) which has a ratchet structure, where one rotating part (e.g., 19-1 in FIG. 12(*d*)) is fixed with the shaft of the drive motor 19 and the other rotating part (e.g., 19-2 in FIG. 12(*d*)) is equipped with (e.g., coupled to) a timing belt 21 and can be mechanically interlocked with the one rotating part 19-1 depending on the rotational direction of the one rotating part 19-1. As shown, the two rotating parts 19-1 and 19-2 may have a same rotational axis and a ratchet mechanism in-between the two rotating parts 19-1 and 19-2, where one rotating part (e.g., rotating part 19-1) is fixed with the shaft of the drive motor 19 and the other rotating part (e.g., rotating part 19-2) equipped with (e.g., coupled to a timing belt 21 can be mechanically interlocked with the one rotating part 19-1 depending on the rotational direction of the one rotating part 19-1. For example, the one rotating part 19-1 attached to the shaft of the drive motor 19 may include movable claws similarly to movable claws 40*c* shown in FIG. 12(*b*) and the other rotating part 19-2 may include grooves similarly to grooves 40*g* shown in FIG. 12(*b*). Besides the claw ratchet structure shown in FIG. 12(*b*), two rotating parts 19-1 and 19-2 may include other ratchet types such as a ball ratchet structure. In some example embodiments, the rotating part may have a ratchet structure as shown in FIGS. 12(*a*) and 12(*b*) and the drive motor side may not have a ratchet structure. In some example embodiments, the drive motor side may have the ratchet structure as shown in FIG. 12(*d*) and the rotating part 23 may not have a ratchet structure. In some example embodiments, the rotating part and the drive motor side may each have a ratchet structure as shown in FIGS. 12(*a*), 12(*b*), and 12(*d*). Accordingly, it will be understood that, in some example embodiments, at least one of the rotating part 23 inside the CT or the drive motor 19 (e.g., one or both of the rotating part 23 and the drive motor 19) includes a separate set of two rotating parts having a same rotational axis (e.g., rotating parts 23-1 and 23-2 in the rotating part and/or rotating parts 19-1 and 19-2 in the drive motor 19) and a respective ratchet mechanism in between (e.g., a first ratchet mechanism may be in between rotating parts 23-1 and 23-2 and/or a separate ratchet mechanism may be in between rotating parts 19-1 and 19-2) wherein the first rotating part (e.g., 19-1, 23-1, etc. and/or 23-1) is configured to be interlocked with the second rotating part (e.g., 19-2, 23-2, etc.) based on the first rotating part rotating in a first rotational direction, and the first rotating part is configured to be released from the second rotating part based on the first rotating part rotating in a decelerated rotational speed, or in an opposite, second rotational direction. The First and second rotational directions for the rotating parts 23-1 and 23-2 may be the same or different from first and second rotational directions for rotating parts 19-1 and 19-2.

FIG. 12(*c*) is a flowchart for explaining a method of driving a CT having a gantry using the ratchet structure shown in FIGS. 12(*a*) and 12 (*b*). Each step (SA1 to SA10) will be described below. It will be understood that the method shown in FIG. 12(*c*) may be performed with regard to any CT according to any of the example embodiments and may be performed, for example, based on operation of a control unit such as control unit 22-1, for example. The method may be performed based on processing circuitry, such as processing circuitry included in and/or implementing the control unit 22-1, executing a program of instructions (e.g., based on a processor of the processing circuitry executing a program of instructions stored in a memory of the processing circuitry). It will be understood that the order of operations (e.g., steps SA1 to SA10) shown in FIG. 12(*c*) may be altered. Operations may be added to and/or removed from the operations of steps SA1 to SA10 of the method as shown in FIG. 12(*c*). As shown in FIG. 12(*c*), the one rotating part 23-1 starts rotating in the direction in which torque is applied to the other rotating part 23-2, and then subsequently or at the same time, the bed or gantry starts moving (SA1). Next, imaging by X-ray irradiation starts (SA2). The digital data obtained from the detector array is wirelessly transmitted to the outside in real time or recorded in the image memory built in the other rotating part 23-2 (SA3). After the end of imaging (SA4), when the rotational torque of the one rotating part 23-1 is reduced or stopped (SA5), the other rotating part 23-2 is released from the mechanical coupling with the one rotating part 23-1 and idles. The energy recovery brake circuit 50 as described in FIG. 11(*d*) is built in the other rotating part 23-2 (not shown in FIG. 12(*c*)), and a counter electromotive force is generated in the induction coil by the rotational kinetic energy. The rotational movement of the other rotating part 23-2 is decelerated while being recovered as electric energy and charging the capacitor and the rechargeable battery (SA6). Then the other rotating part 23-2 is stopped (SA7). Finally, the gantry stops at a particular (or, alternatively, predetermined) position (SA8), the data recorded in the image memory may be read out from the rotating unit interface via the host interface (SA9), and the image is reconstructed in the operation and control unit. After processing, the image information is displayed on the monitor as already explained above. The rechargeable battery can be charged in parallel (SA9), and a series of sequences is completed to enter the standby mode (SA10). With this configuration, the rotational kinetic energy after the completion of imaging is not converted into the rotational motion of the rotating part drive motor 19 via the timing belt 21, but the rotational kinetic energy of the rotating part 23-2 is efficiently harvested and converted into electrical energy by the energy recovery brake circuit 50 without dissipating to the surroundings as Joule heat.

FIG. 13(*a*) is a block diagram for explaining the power supply configuration of a medical vehicle 500 having the vehicle drive motor 77 and the CT according to some example embodiments. The medical vehicle 500 may include a CT according to any of the example embodiments. The medical vehicle 500 includes a hydrogen storage tank 75 which will supply hydrogen gas to the fuel cell 73 (also referred to interchangeably herein as a fuel cell battery) to generate electric energy for vehicle drive motor 77. Further, the medical vehicle 500 has a vehicle energy recovery brake circuit 79 which will regenerate energy associated with the moving vehicle's braking or deceleration. The majority of power for the CT may be supplied from the fuel cell 73 via the gantry table 7. Accordingly, the fuel cell 73 may be understood to be configured to supply electrical power to the CT. Further, the rechargeable battery (e.g., rechargeable battery 27 according to some example embodiments, not shown in FIG. 13(*a*)) inside the gantry 5 can be charged from the vehicle energy recovery brake circuit 79 via the gantry table 7 while the medical vehicle 500 is moving. The solar panel 71, for example, makes it possible to use solar energy and charge the lithium-ion battery 74 inside the vehicle. The fuel cell 73 consumes only hydrogen ($H_2$) and air to emit water ($H_2O$). Problems such as harmful exhaust gas, noise, and vibration may be reduced or even eliminated completely, and then medical activities like a medical examination can be continued without injuring the health of the subject or medical staffs involved.

FIG. 13(*b*) is a schematic view showing a medical vehicle 510, according to some example embodiments. The medical vehicle 510 may include a CT according to any of the example embodiments. In the medical vehicle 500 described according to some example embodiments, the parts for performing the inspection or medical treatment and for driving the vehicle are integrated in one medical vehicle, however as shown in FIG. 13(*b*), the medical vehicle 510 may include driving vehicle 510A and vehicle 510B which may be coupled together as shown, where vehicle 510B may include a CT according to any of the example embodiments and a subject window 20 as shown, and the inspection or medical treatment is performed by the vehicle 510B which may be towed by a separate driving vehicle 510A. In some example embodiments, the vehicle 510B for performing inspection or medical treatment may be supplied electrical energy from either the driving vehicle 510A or the power unit such as a fuel cell equipped in the vehicle 510B. With this configuration, after arriving at the destination, the driving vehicle 510A can separate from the vehicle 510B which will perform the inspection or medical treatment. In some example embodiments, the driving vehicle 510A will pull other vehicles to go to other destinations for performing further inspections or medical treatments.

The medical vehicle 500, 510 facilitates inspections, medical activities by going to remote areas, areas affected by earthquakes, typhoons and developing countries where power supply and refueling cannot be expected. In such environments, it is often expected that the medical vehicle 500, 510 will be moved into an outdoor tent or inside a building such as an evacuation center to continue inspection and medical treatment activities for 24 hours. The energy efficiency of the fuel cell 73 is high, and the spare hydrogen storage tank enables the continuation of medical activities for a longer time.

FIG. 13(*c*) is a flowchart illustrating the medical vehicle 500 operation process including the CT operation according to some example embodiments. Each step (SB1 to SB7) will be described below. It will be understood that the method shown in FIG. 13(*c*) may be performed with regard to any CT according to any of the example embodiments and may be performed, for example, based on operation of a control unit such as control unit 22-1, for example. The method may be performed based on processing circuitry, such as processing circuitry included in and/or implementing the control unit 22-1, executing a program of instructions (e.g., based on a processor of the processing circuitry executing a program of instructions stored in a memory of the processing circuitry). It will be understood that the order of operations (e.g., steps SB1 to SB7) shown in FIG. 13(*c*) may be altered. Operations may be added to and/or removed from the operations of steps SB1 to SB7 of the method as shown in FIG. 13(*c*).

As shown in FIG. 13(*c*), after the medical vehicle 500 starts moving before the medical equipment such as CT will be used at the destination, the fuel cell mainly supplies electric power to the vehicle drive motor but does not need to supply electric power to the medical equipment such as CT (SB1). As described above, the vehicle energy recovery brake circuit is used while the medical vehicle 500 is moving and the rechargeable battery inside the CT can be charged (SB2) since the vehicle energy recovery brake circuit for recovering the energy accompanying the deceleration of the medical vehicle 500 is provided. After the medical vehicle 500 stops at the destination (SB3), the fuel cell mainly supplies electric power to medical equipment such as CT, and it is not necessary to supply electric power to the vehicle drive motor (SB4). The medical activity is completed (SB5). The medical vehicle 500 starts moving (SB6). Then the rechargeable battery built in the CT can be charged by the vehicle energy recovery brake circuit (SB2) until the medical vehicle 500 stops (SB7).

What we call a mobile hospital can be realized based on reducing or minimizing the CT stroke space and using the stabilized electrical power supply means (e.g., power supplies, power sources, etc.) equipped inside a medical vehicle in which the CT is located. Flexible medical services will contribute towards substantiating so-called a 'smart-city.' In addition, even in the cases like hospitals being flooded above floor level due to a torrential rain or a tsunami, expensive medical devices and diagnostic equipment can be evacuated to other locations in advance without any risk of flooding. Combining with the latest AI and high-speed communication technologies, it becomes helpful to support our health maintenance from a much broader perspective without overlooking latent abnormal symptoms in our bodies even in remote places. According to the present inventive concepts, the medical vehicles utilizing the high speed communication system like 5G, and AI based image diagnostics will achieve one-stop medical services in remote or disaster sites, and will reduce not only mental or physical exhaustion of medical staffs but also infection risks due to virus, for example. Example embodiments described above may also contribute to achieve sustainable development goals (SDGs) around the world.

As described herein, any devices, parts, systems, electronic devices, blocks, modules, units, controllers, circuits, and/or portions thereof according to any of the example embodiments, and/or any portions thereof (including, without limitation, control unit 22-1, controller 10-7, controller 12-7, light source drive circuit 29, detector peripheral circuit 33, image memory 35, detector driving and control circuit 41, signal amplifying and analog-to-digital (AD) conversion circuit 43, signal scanning and control circuit 45, digital signal processing circuit 47, parallel to serial conversion circuit 49, an operation and control part as described herein, a data processing unit as described herein, an image drawing circuit as described herein, or the like) may include, may be included in, and/or may be implemented by one or more instances of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), a neural network processing unit (NPU), an Electronic Control Unit (ECU), an Image Signal Processor (ISP), and the like. In some example embodiments, the processing circuitry may include a non-transitory computer readable storage device (e.g., a memory), for example a solid state drive (SSD), storing a program of instructions, and a processor (e.g., CPU) configured to execute the program of instructions to implement the functionality and/or methods performed by some or all of any devices, parts, systems, electronic devices, blocks, modules, units, controllers, circuits, and/or portions thereof according to any of the example embodiments, and/or any portions thereof.

Any of the memories and/or storage devices described herein, including, without limitation, image memory 35, semiconductor image memory 35*m*, or the like, may be a non-transitory computer readable medium and may store a program of instructions. Any of the memories described herein may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM).

Example embodiments having thus been described, it will be obvious that the same may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed:

1. A computer tomographic (CT) system, comprising:

a rotating part having a light source and a rotational central axis;

a fixed part surrounding the rotating part; and a detector array including a plurality of CMOS sensor units, wherein the plurality of CMOS sensor units are arranged inside the rotating part in an arc shape viewed from the rotational central axis, or arranged along an entire inner circumference of the fixed part surrounding the rotational central axis, wherein each CMOS sensor unit of the plurality of CMOS sensor units has a vertical scanning circuit and horizontal scanning and signal readout circuits arranged along at least one side of a rectangular light receiving region, the rectangular light receiving region including a plurality of pixels arranged vertically and horizontally, and a longitudinal direction of the vertical scanning circuit is parallel to a longitudinal direction of the horizontal scanning and signal readout circuits, and wherein each of the longitudinal direction of the vertical scanning circuit and the longitudinal direction of the horizontal scanning and signal readout circuits is perpendicular to the rotational central axis.

2. The CT system of claim 1, wherein, in each CMOS sensor unit, the vertical scanning circuit of the CMOS sensor unit and the horizontal scanning and signal readout circuits of the CMOS sensor unit are at opposite sides of first sides of the rectangular light receiving region of the CMOS sensor unit, such that the plurality of pixels of the rectangular light receiving region of the CMOS sensor unit are arranged vertically and horizontally on opposite sides of second sides of the rectangular light receiving region, the first sides extending in a circumferential direction extending at least partially circumferentially around the rotational central axis, the second sides extending in a rotational central axis direction parallel to the rotational central axis, adjacent CMOS sensor units of the plurality of CMOS sensor units are in contact with each other at a boundary line at least partially defined by respective second sides of the adjacent CMOS sensor units, the boundary line extending parallel to the rotational central axis, the plurality of pixels of each CMOS sensor unit of the adjacent CMOS sensor units include outer pixels adjacent to the boundary line and inner pixels that are spaced apart from the boundary line by at least the outer pixels, and an arrangement pitch in the circumferential direction across the boundary line between an outer pixel of one of the adjacent CMOS sensor units and an outer pixel of another one of the adjacent CMOS sensor units is equal to an arrangement pitch in the circumferential direction between adjacent inner pixels within each of the adjacent CMOS sensor units.

3. The CT system of claim 1, wherein, in each CMOS sensor unit, the vertical scanning circuit of the CMOS sensor unit and the horizontal scanning and signal readout circuits of the CMOS sensor unit are at one side of the rectangular light receiving region of the CMOS sensor unit where the plurality of pixels of the rectangular light receiving region of the CMOS sensor unit are arranged vertically and horizontally on a remaining three sides of the rectangular light receiving region of the CMOS sensor unit, first adjacent CMOS sensor units of the plurality of CMOS sensor units that are adjacent in a circumferential direction extending at least partially circumferentially around the rotational central axis are in contact with each other at a first boundary line that extends in a rotational central axis direction parallel to the rotational central axis, second adjacent CMOS sensor units of the plurality of CMOS sensor units that are adjacent in the rotational central axis direction are in contact with each other at a second boundary line that extends circumferentially along an inner circumference of the rotating part, each CMOS sensor unit includes outer pixels adjacent to at least one boundary line of the first and second boundary lines and inner pixels that are spaced apart from the at least one boundary line by at least the outer pixels, a first arrangement pitch in the circumferential direction between an outer pixel of one of the first adjacent CMOS sensor units and an outer pixel of another one of the first adjacent CMOS sensor units is equal to a second arrangement pitch in the circumferential direction between adjacent inner pixels within each of the first adjacent CMOS sensor units, and a third arrangement pitch in the rotational central axis direction and across the second boundary line between an outer pixel of one of the second adjacent CMOS sensor units and an outer pixel of another one of the second adjacent CMOS sensor units is equal to a fourth arrangement pitch in the rotational central axis direction between adjacent inner pixels within each of the second adjacent CMOS sensor units.

4. The CT system of claim 1, wherein respective longitudinal directions of the plurality of CMOS sensor units are parallel to the rotational central axis.

5. The CT system of claim 1, wherein the plurality of CMOS sensor units are backside illuminated CMOS solid-state image sensors.

6. The CT system of claim 5, wherein the plurality of CMOS sensor units each include a silicon substrate, the silicon substrate having a thickness of 5 microns to 10 microns.

7. The CT system of claim 5, wherein each CMOS sensor unit of the plurality of CMOS sensor units is curved with respect to a direction of incident light.

8. The CT system of claim 5, wherein each CMOS sensor unit of the plurality of CMOS sensor units has a scintillator layer laminated on a backside of the CMOS sensor unit.

9. The CT system of claim 1, wherein the rotating part is inside a gantry, and the CT system further includes the fixed part surrounding the rotating part inside the gantry, the rotating part including the light source, a rechargeable battery, an energy recovery brake circuit, and induction coils that are arranged around an annular part of the rotating part, the fixed part including permanent magnets of N-poles and S-poles facing the induction coils and alternately arranged along the entire inner circumference of the fixed part, or the rotating part is inside a gantry, and the CT system further includes the fixed part surrounding the rotating part inside the gantry, the rotating part including the light source, a rechargeable battery, permanent magnets of N-poles and S-poles alternately arranged along an entire annular part of the rotating part, the fixed part including an energy recovery brake circuit, a seperate rechargeable battery, and induction coils that are arranged along the entire inner circumference of the fixed part facing the permanent magnets of N-poles and S-poles that are alternately arranged around the entire annular part of the rotating part.

10. The CT system of claim 9, wherein the rotating part includes a ratchet structure, such that the rotating part includes two rotating parts having a same rotational axis and a ratchet mechanism in between, the two rotating parts including first and second rotating parts, and the first rotating part is configured to be interlocked with the second rotating part based on the first rotating part rotating in a first rotational direction, and the first rotating part is configured to be released from the second rotating part based on the first rotating part rotating in a decelerated rotational speed, or in an opposite, second rotational direction.

11. The CT system of claim 9, wherein the CT system includes a drive motor that includes a ratchet structure, such that the drive motor includes two rotating parts having a same rotational axis and a ratchet mechanism in between, the two rotating parts including first and second rotating parts, and the first rotating part is configured to be interlocked with the second rotating part based on the first rotating part rotating in a first rotational direction, and the first rotating part is configured to be released from the second rotating part based on the first rotating part rotating in a decelerated rotational speed, or in an opposite, second rotational direction.

12. The CT system of claim 1, further comprising a gantry table, a gantry mounted on the gantry table, and a movable gantry carriage configured to facilitate movement of the gantry in relation to the gantry table in a rotational central axis direction parallel to the rotational central axis.

13. The CT system of claim 1, further comprising a movable bed configured to facilitate movement of a user in a rotational central axis direction parallel to the rotational central axis.

14. A vehicle, comprising the CT system of claim 1.

15. A vehicle, comprising:

an imaging apparatus, the imaging apparatus including an imaging gantry having an inner peripheral; and a subject window in a surface of the vehicle, the subject window configured to be exposed to an exterior of the vehicle via a side face of the vehicle, such that the subject window is configured to enable a subject to enter into or exit from the inner peripheral of the imaging gantry in a body axis direction of the imaging apparatus, wherein the subject window has a central axis that corresponds to a central axis of the inner peripheral of the imaging gantry.

16. The vehicle of claim 15, wherein the imaging apparatus includes a plurality of imaging gantries, the plurality of imaging gantries including the imaging gantry, and separate imaging gantries of the plurality of imaging gantries include different light sources.

17. The vehicle of claim 15, wherein the imaging apparatus includes a plurality of imaging gantries, the plurality of imaging gantries including the imaging gantry, the plurality of imaging gantries including at least one of an X-ray computed tomographic (CT) examination gantry, a positron emission tomography (PET) examination gantry, or a near-infrared diffused light imaging gantry.

18. The vehicle of claim 15, wherein the body axis direction of the imaging apparatus is oriented at a right angle to a direction of a longitudinal axis of the vehicle, and the side face of the vehicle is a left-side face or a right-side face of the vehicle, or the body axis direction of the imaging apparatus is oriented in parallel with the direction of the longitudinal axis of the vehicle, and the side face of the vehicle is a rear-side face of the vehicle.

19. The vehicle of claim 15, wherein the subject window is circular as viewed from the body axis direction of the imaging apparatus.

20. The vehicle of claim 15, wherein the imaging gantry is fixed in relation to the vehicle, or movable along the body axis direction inside the vehicle.

* * * * *